US007166287B1

(12) United States Patent
Highfield et al.

(10) Patent No.: US 7,166,287 B1
(45) Date of Patent: Jan. 23, 2007

(54) VIRAL AGENT

(75) Inventors: Peter E. Highfield, Kent (GB); Brian C. Rodgers, Kent (GB); Richard S. Tedder, Kent (GB); John A. J. Barbara, Hertfordshire (GB)

(73) Assignee: Glaxo Wellcome Inc., Research Triangle Park, NC (US)

( * ) Notice: Subject to any disclaimer, the term of this patent is extended or adjusted under 35 U.S.C. 154(b) by 1095 days.

(21) Appl. No.: 09/664,363

(22) Filed: Sep. 18, 2000

Related U.S. Application Data

(63) Continuation of application No. 08/191,160, filed on Feb. 3, 1994, now Pat. No. 6,210,675, which is a continuation of application No. 07/628,516, filed on Dec. 17, 1990, now abandoned.

(30) Foreign Application Priority Data

| Dec. 18, 1989 | (GB) | ................................... 8928562 |
| Feb. 27, 1990 | (GB) | ................................... 9004414 |
| Mar. 3, 1990 | (GB) | ................................... 9004814 |

(51) Int. Cl.
| A61K 39/29 | (2006.01) |
| A61K 31/7089 | (2006.01) |
| A61K 31/7088 | (2006.01) |
| C12N 15/09 | (2006.01) |
| C12N 15/51 | (2006.01) |
| C12N 15/63 | (2006.01) |
| C12N 15/64 | (2006.01) |
| C12N 5/02 | (2006.01) |

(52) U.S. Cl. .................... 424/184.1; 536/23.1; 514/44; 435/320.1; 435/325; 435/91.1; 435/91.32; 435/91.33; 435/91.4; 435/69.3; 435/6; 424/204.1; 424/228.1; 424/189.1; 424/93.2

(58) Field of Classification Search .............. 424/204.1, 424/228.1, 189.1, 93.2; 536/23.1, 23.72; 435/91.1, 91.32, 91.33, 91.4, 325, 69.1, 69.3, 435/320.1, 6; 514/44
See application file for complete search history.

(56) References Cited

U.S. PATENT DOCUMENTS

| 4,356,164 A | 10/1982 | Tabor et al. |
| 4,673,634 A | 6/1987 | Seto et al. |
| 5,077,193 A | 12/1991 | Mishiro et al. |
| 5,106,726 A | 4/1992 | Wang |
| 5,350,671 A | 9/1994 | Houghton et al. |
| 5,372,928 A | 12/1994 | Miyamura et al. |

FOREIGN PATENT DOCUMENTS

| EP | 058676 | 1/1982 |
| EP | 066296 | 2/1982 |
| EP | 061974 | 10/1982 |
| EP | 092249 | 10/1983 |
| EP | 190972 | 6/1986 |
| EP | 194207 | 9/1986 |
| EP | 242300 | 10/1987 |
| EP | 263761 | 4/1988 |
| EP | 186526 | 7/1988 |
| EP | 277437 | 8/1988 |
| EP | 279460 | 8/1988 |
| EP | 293274 | 11/1988 |
| EP | 0318216 | 5/1989 |
| EP | 88310922 | 5/1989 |
| EP | 335153 | 11/1989 |
| EP | 363025 | 4/1990 |
| EP | 377303 | 7/1990 |
| EP | 0388232 | 9/1990 |
| EP | 419182 | 9/1990 |
| EP | 0398748 | 11/1990 |
| EP | 0414475 | 2/1991 |
| EP | 450931 | 10/1991 |
| GB | 2212511 | 7/1989 |
| WO | 8202774 | 8/1982 |
| WO | 8603498 | 6/1986 |
| WO | 8912462 | 12/1989 |
| WO | 8912641 | 12/1989 |
| WO | 9000597 | 1/1990 |
| WO | 9002206 | 3/1990 |

OTHER PUBLICATIONS

Lechmann et al. Siminars in Liver disease, 2000, vol. 20, pp. 211-226.*
Purcel. Hepatology, 1997, vol. 26(Suppl 1), pp. 11S-14S.*
Lechner et al. Philos. Trans. R. Soc. Lond. B. Bio Sci. 2000, vol. 355, pp. '085-1092.*
Attachment A, GCG word search results for claimed SEQ.ID.'s.
Attachment B, Sequence alignments used for 35 U.S.C. 102 rejections.
Reeck et al, "Homology in Proteins and Nucleic Acids: A Terminology Muddle and a Way out of it", Cell 50:667 (1987).
Miyamura et al, "Detection of antibody against antigen expressed by molecularly cloned hepatitis C virus cDNA: Application to diagnosis and blood screening for posttransfusion hepatitis", Proc. Natl. Acad. Sci. USA 87:983-987 (1990).
Enomoto et al, "There Are Two Major Types of Hepatitis C Virus in Japan", Biochem. Biophys. Res. Commun. 170(3):1021-1025 (1990).
Farci et al, "Lack of Protective Immunity Against Reinfection With Hepatitis C Virus", Science 258:135-140 (1992).
Kirchhausen et al, "Clathrin Heavy Chain . . . ", Proc. Natl. Acad. Sci. USA 84:8805-8809 (1987).
Tordo et al, "Walking Along The Rabies . . . ", Proc. Natl. Acad. Sci. USA 83:3914-3918 (1986).

(Continued)

Primary Examiner—James C. Housel
Assistant Examiner—Bao Qun Li
(74) Attorney, Agent, or Firm—Nixon & Vanderhye P.C.

(57) ABSTRACT

The invention relates to post-transfusional non-A non-B hepatitis viral polypeptide, DNA sequences encoding such viral polypeptide, expression vectors containing such DNA sequences, and hosts transformed by such expression vectors. The invention also relates to the use of such polypeptides in diagnostic assays and vaccine formulations.

16 Claims, 3 Drawing Sheets

OTHER PUBLICATIONS

Figure 1:
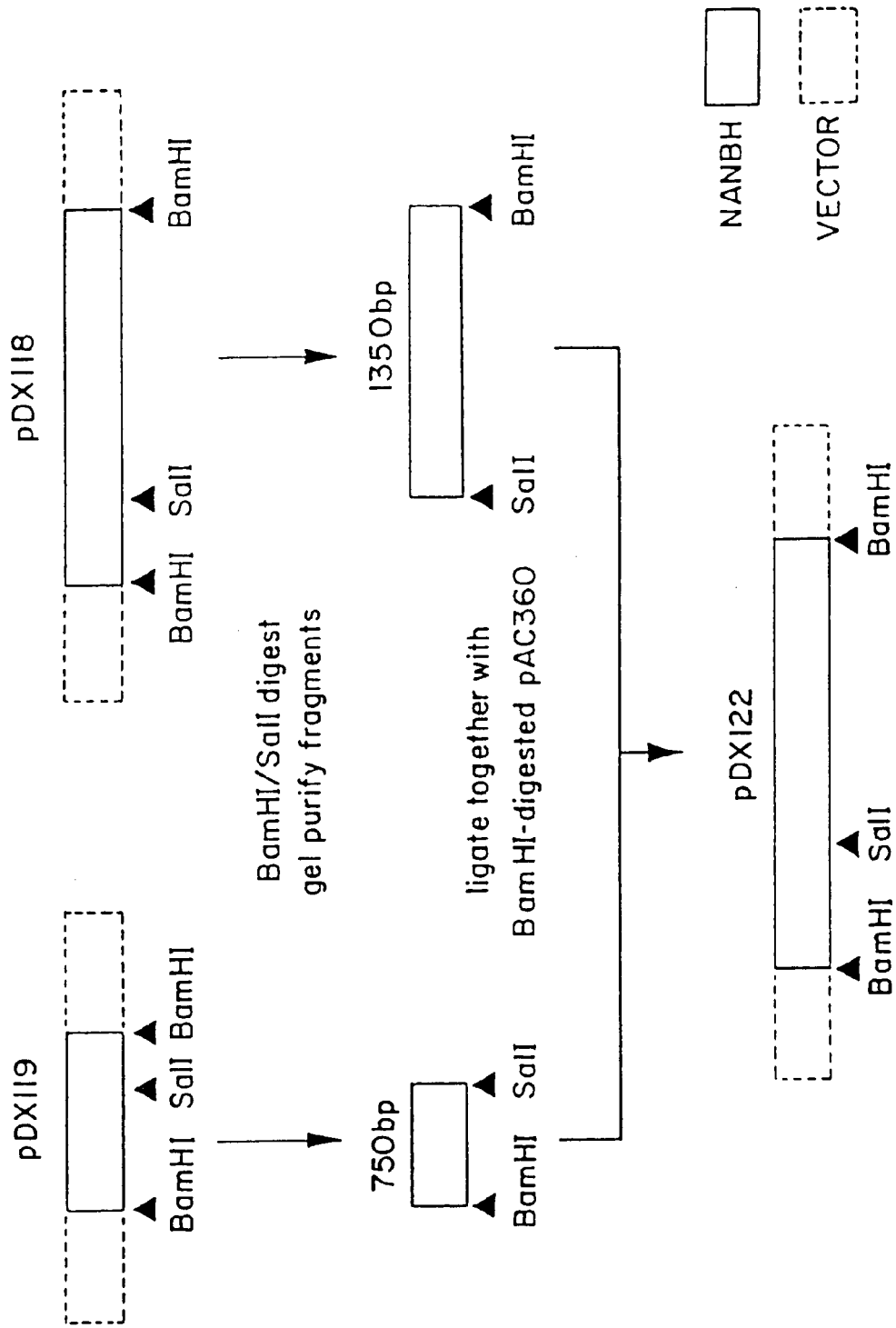

Merson et al., "Molecular Cloning and Sequences . . . ", Virology 167:97-105 (1988).
Geysen et al, "Cognitive Features of . . . ", J. Molec. Recognition 1:32-41 (1988).
Kato et al, "Molecular Cloning of the Human Hepatitis C Virus", Proc. Natl. Acad. Sci. USA 87:9524-9528 (1990).
Shih et al., Progress in Liver Diseases, vol. VIII (1986) 8 pp. 433-452.
Okamoto et al., *Japan J. Exp. Med.* (1990) 60, pp. 167-177.
Bradley et al., Gastroenterology, 88, 773-779 (1985).
Bradley et al., Proc. Natl. Acad. Sci. (USA), 84, 6277-6281 (1987).
Bradley & Maynard, Seminars in Liver Diseases, 6(1), 56-66 (1986).
Iwarson, Brit. Med. J., 295, 946-948 (1987).
He et al., J. Infect. Dis., 156(4), 636-640 (1987).
Nature, 333, May 19, 1988, p. 195.
Choo et al., Science, 244, 359-362 (1989).
Kuo et al., Science, 244, 362-364 (1989).
Esteban et al., The Lancet, 5th Aug. 1989, 294-296.
Van de Poel et al., The Lancet, Aug. 5th, 1989, 297-298.
Kuhnl et al., The Lancet, Aug. 5th, 1989, 324.
Roggendorf et al., The Lancet, Aug. 5th,1989, 324-325.
Maeno et al., Nucleic Acids Res., 18(4), 2685-2689 (1990).
Takeuchi et al., Nucleic Acids Res., 18(15), 4626 (1990).
Takeuchi et al., Gene, 91, 287-291 (1990).
Kubo et al., Nucleic Acids Res., 17(24), 10367-10372 (1989).
Arima et al., Chem. Abs., 112, p. 209 112:1980n (1990).
Gastroenterol. Jpn., 24(5), 540-544 (1989) (abstract only).
Arima et al., Chem. Abs.,112, p. 169 112:49584p (1990).
Gastroenterol. Jpn., 24(5), 545-548 (1989) (abstract only).
Arima et al., chem. Abs., 112, p. 441 112:95311v (1990).
Gastroenterol. Jpn., 24(6), 685-691 (1989) (abstract only).

* cited by examiner

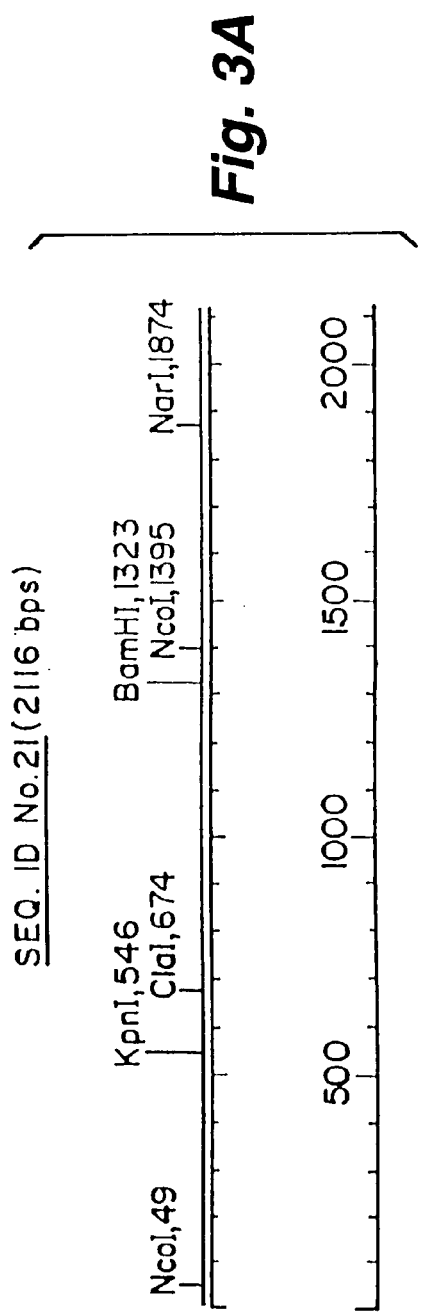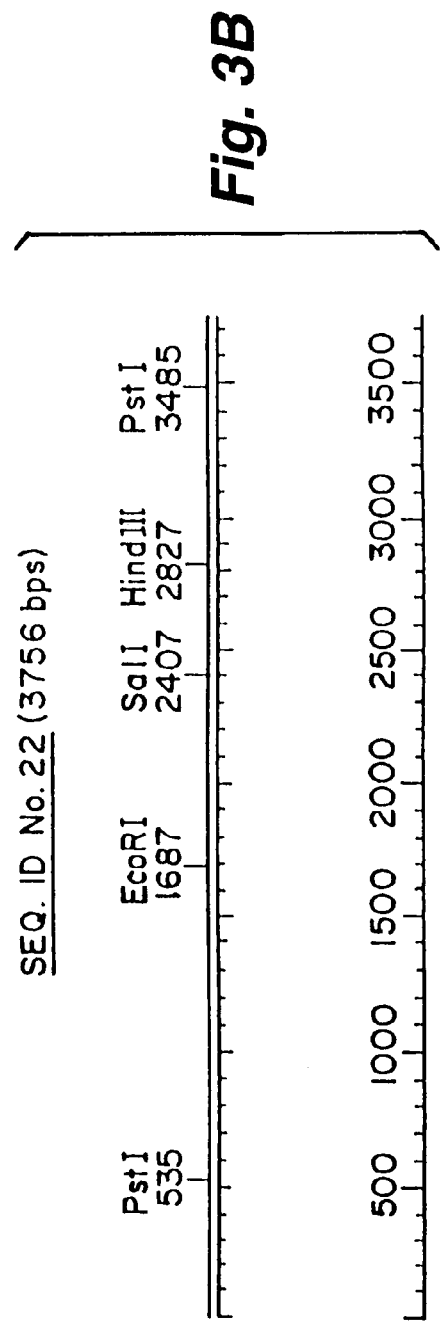

VIRAL AGENT

This application is a continuation of application Ser. No. 08/191,160, filed Feb. 3, 1994, now U.S. Pat. No. 6,210,675, which is a continuation of application Ser. No. 07/628,516, filed Dec. 17, 1990, now abandoned, the entire content of which is hereby incorporated by reference in this application.

The present invention relates to the isolation and characterisation of the viral agent responsible for post-transfusional non-A non-B hepatitis (PT-NANBH) and in particular to PT-NANBH viral polypeptides, DNA sequences encoding such viral polypeptides, expression vectors containing such DNA sequences, and host cells transformed by such expression vectors. The present invention also relates to the use of a DNA sequence in a nucleic acid hybridisation assay for the diagnosis of PT-NANBH. The present invention further relates to the use of PT-NANBH viral polypeptides or polyclonal or monoclonal antibodies against such polypeptides in an immunoassay for the diagnosis of PT-NANBH or in a vaccine for its prevention.

Non-A non-B hepatitis (NANBH) is by definition a diagnosis of exclusion and has generally been employed to describe cases of viral hepatitis infection in human beings that are not due to hepatitis A or B viruses. In the majority of such cases, the cause of the infection has not been identified although, on clinical and epidemiological grounds, a number of agents have been thought to be responsible as reviewed in Shih et al (*Prog. Liver Dis.*, 1986, 8, 433–452). In the USA alone, up to 10% of blood transfusions can result in NANBH which makes it a significant problem. Even for PT-NANBH there may be at least several viral agents responsible for the infection and over the years many claims have been made for the identification of the agent, none of which has been substantiated.

European Patent Application 88310922.5 purports to describe the isolation and characterisation of the aetiological agent responsible for PT-NANBH which is also referred to in the application as hepatitis C virus (HCV). A cDNA library was prepared from viral nucleic acid obtained from a chimpanzee infected with PT-NANBH and was screened using human antisera. A number of positive clones were isolated and sequenced. The resulting nucleic acid and amino acid sequence data, which are described in the application, represent approximately 70% of the 10 kb viral genome and are derived entirely from its 3'-end corresponding to the non-structural coding region.

The present inventors have now isolated and characterised PT-NANBH viral polypeptides by the cloning and expression of DNA sequences encoding such viral polypeptides. Surprisingly, the nucleic acid and amino acid sequence data both show considerable differences with the corresponding data reported in European Patent Application 88310922.5. Overall these differences amount to about 20% at the nucleic acid level and about 15% at the amino acid level but some regions of the sequences show even greater differences. The overall level of difference is much larger than would be expected for two isolates of the same virus even allowing for geographical factors, and is believed to be due to one of two possible reasons.

Firstly, the present inventors and those of the aforementioned European Patent Application used different sources for the nucleic acid used in the cDNA cloning. In particular, the European Patent Application describes the use of chimpanzee plasma as the source for the viral nucleic acid starting material, with the virus having been passaged through a chimpanzee on two occasions. PT-NANBH is of course an human disease and passaging the virus through a foreign host, even if it is a close relative to humans, is likely to result in extensive mutation of the viral nucleic acid. Accordingly, the sequence data contained in European Patent Application 88310922.5 may not be truly representative of the actual viral agent responsible for PT-NANBH in humans. In contrast, the present inventors utilised viral nucleic acid from a human plasma source as the starting material for cDNA cloning. The sequence data thus obtained is much more likely to correspond to the native nucleic acid and amino acid sequences of PT-NANBH.

Secondly, it may be that the viral agent exists as more than one subtype and the sequence data described in the European Patent Application and that elucidated by the present inventors correspond to separate and distinct subtypes of the same viral agent. Alternatively, it may be that the level of difference between the two sets of sequence data is due to a combination of these two factors.

The present invention provides a PT-NANBH viral polypeptide comprising an antigen having an amino acid sequence that is at least 90% homologous with the amino acid sequence set forth in SEQ ID NO: 3,4,5, 18,19,20,21 or 22, or is an antigenic fragment thereof.

SEQ ID NO: 3,4,5,18,19,20,21 or 22 set forth the amino acid sequence as deduced from the nucleic acid sequence. Preferably, the amino acid sequence is at least 95% or even 98% homologous with the amino acid sequence set forth in SEQ ID NO: 3,4,5,18,19,20,21 or 22. Optionally, the antigen may be fused to an heterologous polypeptide.

Two or more antigens may optionally be used together either in combination or fused as a single polypeptide. The use of two or more antigens in this way in a diagnostic assay provides more reliable results in the use of the assay in blood screening for PT-NANBH virus. Preferably, one antigen is obtained from the structural coding region (the 5'-end) and one other antigen is obtained from the non-structural coding region (the 3'-end). It is particularly preferred that the antigens are fused together as a recombinant polypeptide. This latter approach offers a number of advantages in that the individual antigens can be combined in a fixed, predetermined ratio (usually equimolar) and only a single polypeptide needs to be produced, purified and characterised.

An antigenic fragment of an antigen having an amino acid sequence that is at least 90% homologous with that set forth in SEQ ID NO: 3,4,5, 18,19,20,21 or 22 preferably contains a minimum of five, six, seven, eight, nine or ten, fifteen, twenty, thirty, forty or fifty amino acids. The antigenic sites of such antigens may be identified using standard procedures. These may involve fragmentation of the polypeptide itself using proteolytic enzymes or chemical agents and then determining the ability of each fragment to bind to antibodies or to provoke an immune response when inoculated into an animal or suitable in vitro model system (Strohmaier et al, *J. Gen. Virol.*, 1982, 59, 205–306). Alternatively, the DNA encoding the polypeptide may be fragmented by restriction enzyme digestion or other well-known techniques and then introduced into an expression system to produce fragments (optionally fused to a polypeptide usually of bacterial origin). The resulting fragments are assessed as described previously (Spence et al, *J. Gen. Virol.*, 1989, 70, 2843–51; Smith et al, *Gene*, 1984, 29, 263–9). Another approach is to synthesise chemically short peptide fragments (3–20 amino acids long; conventionally 6 amino acids long) which cover the entire sequence of the full-length polypeptide with each peptide overlapping the adjacent peptide. (This overlap can be from 1–10 amino acids but ideally is n-1 amino acids where n is the length of the peptide; Geysen et al, *Proc. Natl. Acad. Sci.*, 1984, 81, 3998–4002). Each peptide is then assessed as described previously except that the peptide is usually first coupled to some carrier molecule to facilitate the induction of an immune response. Finally, there are predictive methods which involve analysis of the sequence for particular features, e.g. hydrophilicity, thought to be associated with immunologically important sites (Hopp and Woods, *Proc. Natl. Acad. Sci.*, 1981, 78, 3824–8; Berzofsky, *Science*, 1985, 229, 932–40). These predictions may then be tested using the recombinant polypeptide or peptide approaches described previously.

Preferably, the viral polypeptide is provided in a pure form, i.e. greater than 90% or even 95% purity.

The PT-NANBH viral polypeptide of the present invention may be obtained using an amino acid synthesiser, if it is an antigen having no more than about thirty residues, or by recombinant DNA technology.

The present invention also provides a DNA sequence encoding a PT-NANBH viral polypeptide as herein defined.

The DNA sequence of the present invention may be synthetic or cloned. Preferably, the DNA sequence is as set forth in SEQ ID NO: 3,4,5,18, 19,20,21 or 22.

To obtain a PT-NANBH viral polypeptide comprising multiple antigens, it is preferred to fuse the individual coding sequences into a single open reading frame. The fusion should of course be carried out in such a manner that the antigenic activity of each antigen is not significantly compromised by its position relative to another antigen. Particular regard should of course be had for the nature of the sequences at the actual junction between the antigens. The methods by which such single polypeptides can be obtained are well known in the art.

The present invention also provides an expression vector containing a DNA sequence, as herein defined, and being capable in an appropriate host of expressing the DNA sequence to produce a PT-NANBH viral polypeptide.

The expression vector normally contains control elements of DNA that effect expression of the DNA sequence in an appropriate host. These elements may vary according to the host but usually include a promoter, ribosome binding site, translational start and stop sites, and a transcriptional termination site. Examples of such vectors include plasmids and viruses. Expression vectors of the present invention encompass both extrachromosomal vectors and vectors that are integrated into the host cell's chromosome. For use in *E. coli*, the expression vector may contain the DNA sequence of the present invention optionally as a fusion linked to either the 5'- or 3'-end of the DNA sequence encoding, for example, β-galactosidase or to the 3'-end of the DNA sequence encoding, for example, the trp E gene. For use in the insect baculovirus (AcNPV) system, the DNA sequence is optionally fused to the polyhedrin coding sequence.

The present invention also provides a host cell transformed with an expression vector as herein defined.

Examples of host cells of use with the present invention include prokaryotic and eukaryotic cells, such as bacterial, yeast, mammalian and insect cells. Particular examples of such cells are *E. coli, S. cerevisiae, P. pastoris*, Chinese hamster ovary and mouse cells, and *Spodoptera frugiperda* and *Tricoplusia* ni. The choice of host cell may depend on a number of factors but, if post-translational modification of the PT-NANBH viral polypeptide is important, then an eukaryotic host would be preferred.

The present invention also provides a process for preparing PT-NANBH viral polypeptide which comprises cloning or synthesising a DNA sequence encoding PT-NANBH viral polypeptide, as herein defined, inserting the DNA sequence into an expression vector such that it is capable in an appropriate host of being expressed, transforming an host cell with the expression vector, culturing the transformed host cell, and isolating the viral polypeptide.

The cloning of the DNA sequence may be carried out using standard procedures known in the art. However, it is particularly advantageous in such procedures to employ the sequence data disclosed herein so as to facilitate the identification and isolation of the desired cloned DNA sequences. Preferably, the RNA is isolated by pelleting the virus from plasma of infected humans identified by implication in the transmission of PT-NANBH. The isolated RNA is reverse transcribed into cDNA using either random or oligo-dT priming. Optionally, the RNA may be subjected to a pre-treatment step to remove any secondary structure which may interfere with cDNA synthesis, for example, by heating or reaction with methyl mercuric hydroxide. The cDNA is usually modified by addition of linkers followed by digestion with a restriction enzyme. It is then inserted into a cloning vector, such as pBR322 or a derivative thereof or the lambda vectors gt10 and gt11 (Huynh et al, *DNA Cloning,* 1985, Vol 1: *A Practical Approach,* Oxford, IRC Press) packaged into virions as appropriate, and the resulting recombinant DNA molecules used to transform *E. coli* and thus generate the desired library.

The library may be screened using a standard screening strategy. If the library is an expression library, it may be screened using an immunological method with antisera obtained from the same plasma source as the RNA starting material and also with antisera from additional human sources expected to be positive for antibodies against PT-NANBH. Since human antisera usually contains antibodies against *E. coli* which may give rise to high background during screening, it is preferable first to treat the antisera with untransformed *E. coli* lysate so as to remove any such antibodies. It is advantageous to employ a negative control using antisera from accredited human donors, i.e. human donors who have been repeatedly tested and found not to have antibodies against viral hepatitis. An alternative screening strategy would be to employ as hybridisation probes one or more labelled oligonucleotides. The use of oligonucleotides in screening a cDNA library is generally simpler and more reliable than screening with antisera. The oligonucleotides are preferably synthesised using the DNA sequence information disclosed herein. One or more additional rounds of screening of one kind or another may be carried out to characterise and identify positive clones.

Having identified a first positive clone, the library may be rescreened for additional positive clones using the first clone as an hybridization probe. Alternatively or additionally, further libraries may be prepared and these may be screened using immunoscreens or hybridisation probes. In this way, further DNA sequences may be obtained.

Alternatively, the DNA sequence encoding PT-NANBH viral polypeptide may be synthesised using standard procedures and this may be preferred to cloning the DNA in some circumstances (Gait, *Oligonucleotide Synthesis: A Practical Approach,* 1984, Oxford, IRL Press).

Thus cloned or synthesised, the desired DNA sequence may be inserted into an expression vector using known and standard techniques. The expression vector is normally cut using restriction enzymes and the DNA sequence inserted using blunt-end or staggered-end ligation. The cut is usually made at a restriction site in a convenient position in the expression vector such that, once inserted, the DNA sequence is under the control of the functional elements of DNA that effect its expression.

Transformation of an host cell may be carried out using standard techniques. Some phenotypic marker is usually employed to distinguish between the transformants that have successfully taken up the expression vector and those that have not. Culturing of the transformed host cell and isolation of the PT-NANBH viral polypeptide may also be carried out using standard techniques.

Antibody specific to a PT-NANBH viral polypeptide of the present invention can be raised using the polypeptide. The antibody may be polyclonal or monoclonal. The antibody may be used in quality control testing of batches of PT-NANBH viral polypeptide; purification of a PT-NANBH viral polypeptide or viral lysate; epitope mapping; when labelled, as a conjugate in a competitive type assay, for antibody detection; and in antigen detection assays.

Polyclonal antibody against a PT-NANBH viral polypeptide of the present invention may be obtained by injecting a PT-NANBH viral polypeptide, optionally coupled to a carrier to promote an immune response, into a mammalian host, such as a mouse, rat, sheep or rabbit, and recovering the antibody thus produced. The PT-NANBH viral polypeptide is generally administered in the form of an injectable formulation in which the polypeptide is admixed with a physiologically acceptable diluent. Adjuvants, such as Freund's complete adjuvant (FCA) or Freund's incomplete adjuvant (FIA), may be included in the formulation. The formulation is normally injected into the host over a suitable period of time, plasma samples being taken at appropriate intervals for assay for anti-PT-NANBH viral antibody. When an appropriate level of activity is obtained, the host is bled. Antibody is then extracted and purified from the blood plasma using standard procedures, for example, by protein A or ion-exchange chromatography.

Monoclonal antibody against a PT-NANBH viral polypeptide of the present invention may be obtained by fusing cells of an immortalising cell line with cells which produce antibody against the viral polypeptide, and culturing the fused immortalised cell line. Typically, a non-human mammalian host, such as a mouse or rat, is inoculated with the viral polypeptide. After sufficient time has elapsed for the host to mount an antibody response, antibody producing cells, such as the splenocytes, are removed. Cells of an immortalising cell line, such as a mouse or rat myeloma cell line, are fused with the antibody producing cells and the resulting fusions screened to identify a cell line, such as a hybridoma, that secretes the desired monoclonal antibody. The fused cell line may be cultured and the monoclonal antibody purified from the culture media in a similar manner to the purification of polyclonal antibody.

Diagnostic assays based upon the present invention may be used to determine the presence or absence of PT-NANBH infection. They may also be used to monitor treatment of such infection, for example in interferon therapy.

In an assay for the diagnosis of viral infection, there are basically three distinct approaches that can be adopted involving the detection of viral nucleic acid, viral antigen or viral antibody. Viral nucleic acid is generally regarded as the best indicator of the presence of the virus itself and would identify materials likely to be infectious. However, the detection of nucleic acid is not usually as straightforward as the detection of antigens or antibodies since the level of target can be very low. Viral antigen is used as a marker for the presence of virus and as an indicator of infectivity. Depending upon the virus, the amount of antigen present in a sample can be very low and difficult to detect. Antibody detection is relatively straightforward because, in effect, the host immune system is amplifying the response to an infection by producing large amounts of circulating antibody. The nature of the antibody response can often be clinically useful, for example IgM rather than IgG class antibodies are indicative of a recent infection, or the response to a particular viral antigen may be associated with clearance of the virus. Thus the exact approach adopted for the diagnosis of a viral infection depends upon the particular circumstances and the information sought. In the case of PT-NANBH, a diagnostic assay may embody any one of these three approaches.

In an assay for the diagnosis of PT-NANBH involving detection of viral nucleic acid, the method may comprise hybridising viral RNA present in a test sample, or cDNA synthesised from such viral RNA, with a DNA sequence corresponding to the nucleotide sequence of SEQ ID NO 3,4,5,18,19,20,21 or 22 and screening the resulting nucleic acid hybrids to identify any PT-NANBH viral nucleic acid. The application of this method is usually restricted to a test sample of an appropriate tissue, such as a liver biopsy, in which the viral RNA is likely to be present at a high level. The DNA sequence corresponding to the nucleotide sequence of SEQ ID NO: 3,4,5,18,19,20,21 or 22 may take the form of an oligonucleotide or a cDNA sequence optionally contained within a plasmid. Screening of the nucleic acid hybrids is preferably carried out by using a labelled DNA sequence. One or more additional rounds of screening of one kind or another may be carried out to characterise further the hybrids and thus identify any PT-NANBH viral nucleic acid. The steps of hybridisation and screening are carried out in accordance with procedures known in the art.

Because of the limited application of this method in assaying for viral nucleic acid, a preferred and more convenient method comprises synthesising cDNA from viral RNA present in a test sample, amplifying a preselected DNA sequence corresponding to a subsequence of the nucleotide sequence of SEQ ID NO: 3,4,5,18,19,20,21 or 22, and identifying the preselected DNA sequence. The test sample may be of any appropriate tissue or physiological fluid and is preferably concentrated for any viral RNA present. Examples of an appropriate tissue include a liver biopsy. Examples of an appropriate physiological fluid include urine, plasma, blood, serum, semen, tears, saliva or cerebrospinal fluid. Preferred examples are serum and plasma.

Synthesis of the cDNA is normally carried out by primed reverse transcription using random, defined or oligo-dT primers. Advantageously, the primer is an oligonucleotide corresponding to the nucleotide sequence of SEQ ID NO: 3,4,5,18,19,20,21 or 22 and designed to enrich for cDNA containing the preselected sequence.

Amplification of the preselected DNA sequence is preferably carried out using the polymerase chain reaction (PCR) technique (Saiki et al, *Science,* 1985, 230, 1350–4). In this technique, a pair of oligonucleotide primers is employed one of which corresponds to a portion of the nucleotide sequence of SEQ ID NO: 3,4,5,18,19,20,21 or 22 and the other of which is located to the 3' side of the first and corresponds to a portion of the complementary sequence, the pair defining between them the preselected DNA sequence. The oligonucleotides are usually at least 15, optimally 20 to 26, bases long and, although a few mismatches can be tolerated by varying the reaction conditions, the 3'-end of the oligonucleotides should be perfectly complementary so as to prime effectively. The distance between the 3'-ends of the oligonucleotides may be from about 100 to about 2000 bases. Conveniently, one of the pair of oligonucleotides that is used in this technique is also used to prime cDNA synthesis. The PCR technique itself is carried out on the cDNA in single stranded form using an enzyme, such as Taq polymerase, and an excess of the oligonucleotide primers over 20–40 cycles in accordance with published protocols (Saiki et al, *Science,* 1988, 239, 487–491).

As a refinement of the technique, there may be several rounds of amplification, each round being primed by a different pair of oligonucleotides. Thus, after the first round of amplification, an internal pair of oligonucleotides defining a shorter DNA sequence (of, say, from 50 to 500 bases long) may be used for a second round of amplification. In this somewhat more reliable refinement, referred to as 'Nested PCR', it is of course the final amplified DNA sequence that constitutes the preselected sequence. (Kemp et al, *Proc. Natl. Acad. Sci.,* 1989, 86(7), 2423-7 and Mullis et al, *Methods in Enzymology,* 1987, 155, 335–350).

Identification of the preselected DNA sequence may be carried out by analysis of the PCR products on an agarose gel. The presence of a band at the molecular weight calculated for the preselected sequence is a positive indicator of viral nucleic acid in the test sample. Alternative methods of identification include those based on Southern blotting, dot blotting, oligomer restriction and DNA sequencing.

The present invention also provides a test kit for the detection of PT-NANBH viral nucleic acid, which comprises
i) a pair of oligonucleotide primers one of which corresponds to a portion of the nucleotide sequence of SEQ ID NO: 3,4,5,18,19,20,21 or 22 and the other of which is located to the 3' side of the first and corresponds to a portion of the complementary sequence, the pair defining between them a preselected DNA sequence;
ii) a reverse transcriptase enzyme for the synthesis of cDNA from test sample RNA upstream of the primer corresponding to the complementary nucleotide sequence of SEQ ID NO 3,4,5,18,19,20,21 or 22;
iii) an enzyme capable of amplifying the preselected DNA sequence; and optionally;
iv) washing solutions and reaction buffers.

Advantageously, the test kit also contains a positive control sample to facilitate in the identification of viral nucleic acid.

The characteristics of the primers and the enzymes are preferably as described above in connection with the PCR technique.

In an assay for the diagnosis of PT-NANBH involving detection of viral antigen or viral antibody, the method may comprise contacting a test sample with a PT-NANBH viral polypeptide of the present invention, or polyclonal or monoclonal antibody against the polypeptide, and determining whether there is any antigen-antibody binding contained within the test sample. For this purpose, a test kit may be provided comprising a PT-NANBH viral polypeptide, as defined herein, or a monoclonal or polyclonal antibody thereto, and means for determining whether there is any binding with antibody or antigen respectively contained in the test sample. The test sample may be taken from any of the appropriate tissues and physiological fluids mentioned above for the detection of viral nucleic acid. If a physiological fluid is obtained, it may optionally be concentrated for any viral antigen or antibody present.

A variety of assay formats may be employed. The PT-NANBH viral polypeptide can be used to capture selectively antibody against PT-NANBH from solution, to label selectively the antibody already captured, or both to capture and label the antibody. In addition, the viral polypeptide may be used in a variety of homogeneous assay formats in which the antibody reactive with the antigen is detected in solution with no separation of phases.

The types of assay in which the PT-NANBH viral polypeptide is used to capture antibody from solution involve immobilization of the polypeptide onto a solid surface. This surface should be capable of being washed in some way. Examples of suitable surfaces include polymers of various types (moulded into microtitre wells; beads; dipsticks of various types; aspiration tips; electrodes; and optical devices), particles (for example latex; stabilized red blood cells; bacterial or fungal cells; spores; gold or other metallic or metal-containing sols; and proteinaceous colloids) with the usual size of the particle being from 0.02 to 5 microns, membranes (for example of nitrocellulose; paper; cellulose acetate; and high porosity/high surface area membranes of an organic or inorganic material).

The attachment of the PT-NANBH viral polypeptide to the surface can be by passive adsorption from a solution of optimum composition which may include surfactants, solvents, salts and/or chaotropes; or by active chemical bonding. Active bonding may be through a variety of reactive or activatible functional groups which may be exposed on the surface (for example condensing agents; active acid esters, halides and anhydrides; amino, hydroxyl, or carboxyl groups; sulphydryl groups; carbonyl groups; diazo groups; or unsaturated groups). Optionally, the active bonding may be through a protein (itself attached to the surface passively or through active bonding), such as albumin or casein, to which the viral polypeptide may be chemically bonded by any of a variety of methods. The use of a protein in this way may confer advantages because of isoelectric point, charge, hydrophilicity or other physico-chemical property. The viral polypeptide may also be attached to the surface (usually but not necessarily a membrane) following electrophoretic separation of a reaction mixture, such as immune precipitation.

After contacting (reacting) the surface bearing the PT-NANBH viral polypeptide with a test sample, allowing time for reaction, and, where necessary, removing the excess of the sample by any of a variety of means, (such as washing, centrifugation, filtration, magnetism or capilliary action) the captured antibody is detected by any means which will give a detectable signal. For example, this may be achieved by use of a labelled molecule or particle as described above which will react with the captured antibody (for example protein A or protein G and the like; anti-species or anti-immunoglobulin-sub-type; rheumatoid factor; or antibody to the antigen, used in a competitive or blocking fashion), or any molecule containing an epitope contained in the polypeptide.

The detectable signal may be optical or radioactive or physico-chemical and may be provided directly by labelling the molecule or particle with, for example, a dye, radiolabel, electroactive species, magnetically resonant species or fluorophore, or indirectly by labelling the molecule or particle with an enzyme itself capable of giving rise to a measurable change of any sort. Alternatively the detectable signal may be obtained using, for example, agglutination, or through a diffraction or birefringent effect if the surface is in the form of particles.

Assays in which a PT-NANBH viral polypeptide itself is used to label an already captured antibody require some form of labelling of the antigen which will allow it to be detected. The labelling may be direct by chemically or passively attaching for example a radio label, magnetic resonant species, particle or enzyme label to the polypeptide; or indirect by attaching any form of label to a molecule which will itself react with the polypeptide. The chemistry of bonding a label to the PT-NANBH viral polypeptide can be directly through a moiety already present in the polypeptide, such as an amino group, or through an intermediate moiety, such as a maleimide group. Capture of the antibody may be on any of the surfaces already mentioned by any reagent including passive or activated adsorption which will result in specific antibody or immune complexes being bound. In particular, capture of the antibody could be by anti-species or anti-immunoglobulin-sub-type, by rheumatoid factor, proteins A, G and the like, or by any molecule containing an epitope contained in the polypeptide.

The labelled PT-NANBH polypeptide may be used in a competitive binding fashion in which its binding to any specific molecule on any of the surfaces exemplified above is blocked by antigen in the sample. Alternatively, it may be used in a non-competitive fashion in which antigen in the sample is bound specifically or non-specifically to any of the surfaces above and is also bound to a specific bi- or poly-valent molecule (e.g. an antibody) with the remaining valencies being used to capture the labelled polypeptide.

Often in homogeneous assays the PT-NANBH viral polypeptide and an antibody are separately labelled so that, when the antibody reacts with the viral polypeptide in free solution, the two labels interact to allow, for example, non-radiative transfer of energy captured by one label to the other label with appropriate detection of the excited second label or quenched first label (e.g. by fluorimetry, magnetic resonance or enzyme measurement). Addition of either viral polypeptide or antibody in a sample results in restriction of the interaction of the labelled pair and thus in a different level of signal in the detector.

A suitable assay format for detecting PT-NANBH antibody is the direct sandwich enzyme immunoassay (EIA) format. A PT-NANBH viral polypeptide is coated onto microtitre wells. A test sample and a PT-NANBH viral polypeptide to which an enzyme is coupled are added simultaneously. Any PT-NANBH antibody present in the test sample binds both to the viral polypeptide coating the well and to the enzyme-coupled viral polypeptide. Typically, the same viral polypeptide is used on both sides of the sandwich. After washing, bound enzyme is detected using a specific substrate involving a colour change. A test kit for use in such an EIA comprises:

(1) a PT-NANBH viral polypeptide labelled with an enzyme;

(2) a substrate for the enzyme;

(3) means providing a surface on which a PT-NANBH viral polypeptide is immobilised; and (4) optionally, washing solutions and/or buffers.

The viral polypeptides of the present invention may be incorporated into a vaccine formulation for inducing immunity to PT-NANBH in man. For this purpose the viral polypeptide may be presented in association with a pharmaceutically acceptable carrier.

For use in a vaccine formulation, the viral polypeptide may optionally be presented as part of an hepatitis B core fusion particle, as described in Clarke et al (*Nature,* 1987, 330, 381–384), or a polylysine based polymer, as described in Tam (*PNAS,* 1988, 85, 5409–5413). Alternatively, the viral polypeptide may optionally be attached to a particulate structure, such as liposomes or ISCOMS.

Pharmaceutically acceptable carriers include liquid media suitable for use as vehicles to introduce the viral polypeptide into a patient. An example of such liquid media is saline solution. The viral polypeptide itself may be dissolved or suspended as a solid in the carrier.

The vaccine formulation may also contain an adjuvant for stimulating the immune response and thereby enhancing the effect of the vaccine. Examples of adjuvants include aluminium hydroxide and aluminium phosphate.

The vaccine formulation may contain a final concentration of viral polypeptide in the range from 0.01 to 5 mg/ml, preferably from 0.03 to 2 mg/ml. The vaccine formulation may be incorporated into a sterile container, which is then sealed and stored at a low temperature, for example 4° C., or may be freeze-dried.

In order to induce immunity in man to PT-NANBH, one or more doses of the vaccine formulation may be administered. Each dose may be 0.1 to 2 ml, preferably 0.2 to 1 ml. A method for inducing immunity to PT-NANBH in man, comprises the administration of an effective amount of a vaccine formulation, as hereinbefore defined.

The present invention also provides the use of a PT-NANBH viral polypeptide in the preparation of a vaccine for use in the induction of immunity to PT-NANBH in man.

Vaccines of the present invention may be administered by any convenient method for the administration of vaccines including oral and parenteral (e.g. intravenous, subcutaneous or intramuscular) injection. The treatment may consist of a single dose of vaccine or a plurality of doses over a period of time.

The following transformed strains of *E. coli* were deposited with the National Collection of Type Cultures (NCTC), Central Public Health Laboratory, 61, Colindale Avenue, London, NW9 5HT on the indicated dates:

i) *E. coli* TG1 transformed by pDX113 (WD001); Deposit No. NCTC 12369; 7 Dec. 1989 ii) *E. coli* TG1 transformed by pDX128 (WD002); Deposit No. NCTC 12382; 23 Feb. 1990.

iii) *E. coli* TG1 transformed by p136/155 (WD003); Deposit No. NCTC 28 Nov. 1990.

iv) *E. coli* TG1 transformed by p156/92 (WD004); Deposit No. NCTC 28 Nov. 1990.

v) *E. coli* TG1 transformed by p129/164 (WD005); Deposit No. NCTC 28 Nov. 1990.

vi) *E. coli* TG1 transformed by pDX136 (WD006); Deposit No. NCTC 28 Nov. 1990.

BRIEF DESCRIPTION OF THE DRAWINGS

In the Figures,

FIG. 1 shows a representation of the production of pDX122 described in Example 7, FIG. 2 shows a representation of the production of two alternative fused sequences described in Example 17, and FIGS. 3A and 3B show restriction maps of SEQ ID NO: 21 and 22.

In the Sequence Listing, there are listed SEQ ID NO: 1 to 25 to which references are made in the description and claims.

The following Examples serve to illustrate the invention.

EXAMPLE 1

Synthesis of cDNA

Pooled plasma (160 mls) from two individuals (referred to as A and L) known to have transmitted NANBH via transfusions was diluted (1:2.5) with phosphate buffered saline (PBS) and then centrifuged at 190,000 g (e.g. 30,000 rpm in an MSE 8×50 rotor) for 5hrs at 4° C. The supernatant was retained as a source of specific antibodies for subsequent screening of the cDNA libraries. The pellet was resuspended in 2 mls of 20 mM tris-hydrochloride, 2 mM EDTA 3% SDS, 0.2M NaCl (2×PK) extracted 3 times with an equal volume of phenol, 3 times with chloroform, once with ether, and then precipitated with 2.5 volumes of ethanol at −20° C. The precipitate was resuspended in 10 µl of 10 mM tris-hydrochloride, 1 mM EDTA at pH 8.0 (TE).

The nucleic acid was used as a template in a cDNA synthesis kit (Amersham International plc, Amersham, U.K.) with both oligo-dT and random hexanucleotide priming. The reaction conditions were as recommended by the kit supplier. Specifically, 1 ul of the nucleic acid was used for a first strand synthesis reaction which was labelled with [α-$^{32}$P]dCTP (Amersham; specific activity 3000 Ci/mmol) in a final volume of 20 ul and incubated at 42° C. for 1 hour. The entire first strand reaction was then used for second strand synthesis reaction, containing E. coli RNaseH (0.8 U) and DNA polymerase I (23 U) in a final volume of 100 ul, incubated at 12° C. for 60 minutes then 22° C. for 60 minutes. The entire reaction was then incubated at 70° C. for 10 minutes, placed on ice, 1 U of T4 DNA polymerase was added and then incubated at 37° C. for 10 minutes. The reaction was stopped by addition of 5 ul of 0.2M EDTA pH8.

Unincorporated nucleotides were removed by passing the reaction over a NICK column (Pharmacia Ltd, Milton Keynes, U.K.) The cDNA was than extracted twice with phenol, three times with chloroform, once with ether and then 20 µg dextran was added before precipitation with 2.5 volumes of 100% ethanol.

EXAMPLE 2

Production of Expression Libraries

The dried cDNA pellet was resuspended in 5 ul of sterile TE and then incubated with 500 ng of EcoRI linkers (Pharmacia; GGAATTCC phosphorylated) and 0.5 U of T4 DNA ligase (New England BioLabs, Beverley, Mass., USA) in final volume of 10 µl containing 20 mM Tris-HCl pH7.5, 10 mM MgCl$_2$, 10 mM DTT, 1 mM ATP for 3 hours at 15° C. The ligase was inactivated by heating to 65° C. for 10 minutes and the cDNA was digested with 180U of EcoRI (BCL, Lewes, U.K.) in a final volume of 100 µl at 37° C. for 1 hour. EDTA was added to a final concentration of 10 mM and the entire reaction loaded onto an AcA34 (LKB) column. Fractions (50 µl) were collected and counted. The peak of cDNA in the excluded volume (980 cpm) was pooled, extracted twice with phenol, three times with chloroform, once with ether and then ethanol precipitated.

The ds cDNA was resuspended in 5 µl TE and ligated onto lambda gt11 EcoRI arms (Gibco, Paisley, Scotland) in a 10 µl reaction containing 0.5U T4 DNA ligase, 66 mM tris-hydrochloride, 10 mM MgCl$_2$, 15 mM DTT pH 7.6 at 15° C. overnight. After inactivating the ligase by heating to 65° C. for 10 minutes, 5 ul of the reaction were added to an Amersham packaging reaction and incubated at 22° C. for 2 hours. The packaged material was titrated on E. coli strain Y1090 (Huynh et al 1985) and contained a total of 2.6×10$^4$ recombinants.

Plating cells (Y1090) were prepared by inoculating 10 mls L-broth with a single colony from an agar plate and shaking overnight at 37° C. The next day 0.5 mls of the overnight culture were diluted with 10 mls of fresh L-broth and 0.1 ml 1M MgSO$_4$ and 0.1 ml 20% (w/v) maltose were added. The culture was shaken for 2 hours at 37° C., the bacteria harvested by centrifugation at 5,000 g for 10 minutes and resuspended in 5 mls 10 mM MgSO$_4$ to produce the plating cell stock. A portion (1 ul) of the packed material was mixed with 0.2 ml of plating cells, incubated at 37° C. for 20 minutes before 3 mls of top agar were added and the entire mixture poured onto a 90 mm L-agar plate. After overnight incubation at 37° C. plaques were counted and the total number of recombinant phage determined. The remaining packaged material (500 ul) was stored at 4° C.

Additional libraries were prepared in a substantially similar manner.

EXAMPLE 3

Screening of Expression Libraries

The initial library described in Example 2 was plated out onto E. coli strain Y1090 at a density of about 5×10$^3$ pfu per 140 mm plate and grown at 37° C. for 2 hours until the plaques were visible. Sterile nitrocellulose filters which had been impregnated with IPTG (isopropylthiogalactoside) were left in contact with the plate for 3 hours and then removed. The filters were first blocked by incubation with blocking solution [3% (w/v)BSA/TBS-Tween(10 mM Tris-HCl pH8, 150 mM NaCl, 0.05% (v/v) Tween 20) containing 0.05% bronidox] (20 mls/filter) and then transferred to binding buffer [1% (w/v)BSA/TBS/Tween containing 0.05% bronidox] containing purified (by ion-exchange chromatography) antibodies from pooled A & L plasma (20 µg/ml). After incubation at room temperature for 2 hours the filters were washed three times with TBS-Tween and then incubated in binding buffer containing biotinylated sheep anti-human (1:250). After 1 hour at room temperature the filters were washed 3 times with TBS/Tween and then incubated in binding buffer containing streptavidin/peroxidase complex (1:100). The signal developed with DAB. Positive signals appeared as (coloured) plaques.

Out of a total of 2.6×10$^4$ plaques screened, 8 positives were obtained on the first round screen. Using the filters as a template, the regions of the original plates corresponding to these positive signals were picked off using a sterile pasteur pipette. The agar plugs were suspended in 0.1 ml of SM buffer and the phage allowed to diffuse out. The titre of phage from each plug was determined on E. coli strain Y1090. The phage stock from each plug was then re-screened as before on individual 90 mm plates at a density of about 1×10$^3$ pfu per plate. Of 8 first round positives, one was clearly positive on the second round, i.e. >1% of plaques positive, this was called JG2. This corresponds to a positive rate of 40/10$^6$ in the library.

This and other positive phage identified in an similar way from other cDNA libraries described in Example 2 were then purified by repeated rounds of plaque screening at lower density (1–200 pfu/90 mm plate) until 100% of the plaques were positive with the A&L antibody screen. Three such recombinant phage were JG1, JG2 and JG3.

EXAMPLE 4

Secondary Screening of JG1, JG2 and JG3 with Serum Panels

Each of the recombinant phage, JG1, JG2 and JG3, were plaque purified and stored as titred stocks in SM buffer at 4° C. These phage were mixed (1:1) with a stock of phage identified as negative in Example 3 and mixture used to infect E. coli strain Y1090 at 1000 pfu per plate. Plaque lifts were taken and processed as described in Example 3 except that the filters were cut into quadrants and each quadrant was incubated with a different antibody; these were A&L antibodies (20 µg/ml); A plasma (1:500); L plasma (1:500) and H IgG (20 µg/ml). H is a patient expected to be positive for PT-NANBH antibodies because he was a haemophiliac who had received non-heat-treated Factor VIII. At the end of the reaction each filter was scored blind as positive (when there were clearly two classes of signal) or negative (when all plaques gave the same signal). This could be a subjective judgement and so the scores were compared and only those filters where there was a majority agreement were taken as positive. The results are presented in Table 1.

TABLE 1

|  | A&L | A | L | H |
|---|---|---|---|---|
| JG1 | + | + | − | − |
| JG2 | + | + | + | + |
| JG3 | + | + | + | + |

JG1 appeared only to react with antibodies from patient A and not L or H; this is not what would be expected of a true PT-NANBH related recombinant polypeptide and so JG1 was dropped from the analysis. However both JG2 and JG3 gave clear positive reactions with three PT-NANBH sera A, L and H; these were analysed further.

The type of analysis described above was repeated for JG2 and JG3 except that the filters were cut into smaller portions and these were incubated with panels of positive and negative sera. The panels of positive sera comprised one panel of 10 haemophiliac sera and one panel of 9 intravenous drug addict (IVDA) sera. These represented the best source of positive sera even though the actual positive rate was unknown. The panel of negative sera was obtained from accredited donors who have been closely monitored over many years by the North London Blood Transfusion Centre, Deansbrook Road, Edgware, Middlesex, U.K. and have never shown any sign of infection with a variety of agents including PT-NANBH. The results are presented in Tables 2 & 3.

TABLE 2

|  | I.D. | JG2 | JG3 |
|---|---|---|---|
| IVDAs | V19146 | 4/4 | 0/5 |
|  | V27083 | 2/4 | 0/5 |
|  | V29779 | 0/4 | 0/5 |
|  | V12561 | 0/5 | 4/5 |
|  | V15444 | 3/4 | 5/5 |
|  | V18342 | 4/4 | 0/5 |
|  | V8403 | 3/4 | 0/5 |
|  | V20001 | 4/4 | 0/5 |
|  | V21213 | 3/4 | 0/5 |
| Haemophiliacs | M1582 | 4/4 | 4/5 |
|  | M1581 | 5/5 | 5/5 |
|  | M1575 | 3/5 | 0/5 |
|  | M1579 | 5/5 | 5/5 |
|  | M1585 | 3/5 | 0/5 |
|  | M1576 | 1/5 | 1/5 |
|  | M1580 | 1/5 | 0/5 |
|  | M1578 | 1/5 | 0/5 |
|  | M1587 | 1/5 | 3/5 |
|  | M1577 | 2/5 | 1/5 |

Positives are underlined.

TABLE 3

|  | IVDA | Haemophiliac | Accredited Donor |
|---|---|---|---|
| JG2 | 6/9(66%) | 5/10(50%) | 0/10(0%) |
| JG3 | 2/9(22%) | 4/10(40%) | 0/10(0%) |

TABLE 3-continued

|  | IVDA | Haemophiliac | Accredited Donor |
|---|---|---|---|
| JG2 + JG3 | 1/9(11%) | 3/10(30%) | 0/10(0%) |
| JG2 or JG3 | 7/9(77%) | 6/10(60%) | 0/10(0%) |

These data are consistent with the hypothesis that both recombinants are expressing polypeptides associated with an agent responsible for PT-NANBH and that these polypeptides are not identical but may share some antigenic sites.

EXAMPLE 5

Restriction Mapping and DNA Sequencing of JG2 and JG3

A portion (10 µl) of the phage stocks for both JG2 and JG3 was boiled to denature the phage and expose the DNA. This DNA was then used as a template in a PCR amplification using Taq polymerase; each reaction contained the following in a final volume of 50 ul:–10 mM Tris-HCl, 50 mM KCl, 1.5 mM $MgCl_2$, 0.01% gelatin, pH 8.3 at 25° C. plus oligonucleotide primers d19 and d20 (SEQ ID NO: 1 and 2 respectively; 200 ng each); these primers are located in the lambda sequences flanking the Eco RI cloning site and therefore prime the amplification of anything cloned into this site.

A portion of the reaction was analysed on a 1.0% agarose gel and compared to markers. Amplification of JG2 produced a fragment of approximately 2 Kb; JG3 one of approximately 1 Kb. The remaining reaction mix was extracted with phenol/chloroform in the presence of 10 mM EDTA and 1% SDS and the DNA recovered by ethanol precipitation. The amplified material was then digested with 20U of EcoRI for 60 minutes at 37° C. and separated on a 1.0% LGT agarose gel in TAE. The fragments were reduced in size as expected and were eluted and purified using Elutips (S&S). The JG2 and JG3 inserts were ligated with EcoRI digested pUC13 and transformed into E. coli strain TG1. Recombinants were identified as white colonies on X-gal/L-Amp plates (L-Agar plates supplemented with 100 µg/ml ampicillin, 0.5 mg/ml X-gal) and were checked by small-scale plasmid preparations and EcoRI restriction enzyme digestion to determine the size of the insert DNA. The recombinant plasmid containing the JG2 insert was called DM415 and that containing the JG3 insert was called DM416.

The sequence of the JG2 insert was determined by direct double-stranded sequencing of the plasmid DNA and by subcloning into M13 sequencing vectors such as mp18 and mp19 followed by single-stranded sequencing. The sequence of the JG3 insert was similarly determined. The resulting DNA and deduced aminoacid sequences are set forth in SEQ ID NO: 3 and 4.

EXAMPLE 6

Expression of PT-NANBH Polypeptide in E. coli

The plasmid pDM416 (5 ug) was digested with EcoRI (20U) in a final volume of 20 ul and the 1 Kb insert recovered by elution from a 1% LGT agarose gel. This material was then "polished" using Klenow fragment and a DNTP mix to fill in the EcoRI overhanging ends. The DNA was recovered by ethanol precipitation following extraction with phenol/chloroform. The blunt-ended fragment was ligated into SmaI cleaved/phosphatased pDEV107 (a vector which permits cloning at the 3' end of lac Z) and then transformed into *E. coli* TG1 cells. There was a 30-fold increase in colonies over a vector-alone control. Transformants containing the required recombinant plasmid were identified by hybridisation with a radioactive probe produced by PCR amplification of the JG3 recombinant. Twelve colonies were analysed by restriction enzyme digestion (SalI) of plasmid mini-preparations to determine the orientation of the insert. A quarter of these recombinants were in the correct orientation to express the PT-NANBH sequence as a fusion with β-galactosidase. One of these (pDX113) was taken for further analysis.

A colony of pDX113 was used to inoculate 50 mls L-broth, grown at 37° C. with shaking to mid-log phase and expression induced by addition of 20 mM IPTG. After 3 hours the cells were harvested by centrifugation at 5,000 g for 20 minutes, resuspended in 50 mls PBS and repelleted. The pelleted cells were resuspended in 5 mls of buffer (25 mM Tris-HCl, 1 mM EDTA, 1 mg/ml lysozyme, 0.2% (v/v) Nonidet-P40, pH8.0) per gram of pellet and incubated at 0° C. for 2 hours. The released bacterial DNA was digested by addition of DNase I and $MgSO_4$ to final concentrations of 40 ug/ml and 2 mM respectively to reduce viscosity.

This crude lysate was analysed by PAGE and the pattern of proteins stained with Coomassie blue. A protein of approximately 150 kD was induced in bacteria containing pDX113 and this protein was estimated to account for 10–15% of the total protein. Similar gels were transferred to PVDF membrane (CR1, Dunmow, Essex, U.K.) and the membranes incubated with PT-NANBH-positive and negative sera; the 150 kD protein reacted with the A and L sera but not normal human serum. Control tracks containing lysate from *E. coli* expressing β-galactosidase did not react with A, L or normal human sera.

Urea was added to the crude lysate to a final concentration of 6M and insoluble material removed by centrifugation. The 6M urea extract was used to coat microtitre wells directly for 1 hour at 37° C. The wells were washed three times with double-distilled water and then blocked by addition of 0.25 ml of 0.2% BSA per well containing 0.02% $NaN_3$ for 20 minutes at 37° C. The plate was then aspirated. Control plates coated with a crude lysate of a β-galactosidase-producing *E. coli* strain (pXY461) were produced in the same way. These plates were used in ELISA assays as described in Example 10.

EXAMPLE 7

Expression of PT-NANBH Polypeptide in Insect Cells

The PT-NANBH insert from JG3, isolated as described in Example 5, was cloned in-frame with the first 34 nucleotides of polyhedrin in the vector pAc360 (Luckow and Summers, *Biotechnology*, 1988, 6, 47–55), utilising our knowledge of the reading frame of the lacZ gene in the gt11 vector. Oligonucleotides were synthesised which were able to hybridise to gt11 sequences flanking the EcoRI cloning site and which would enable the amplification of the insert by PCR. These oligonucleotides included BamHI restriction sites suitably placed to allow direct cloning into the BamHI site of pAc360, placing the inserted gene in-frame with the amino terminal sequences of polyhedrin.

A small amount of the gt11 recombinant JG3 was boiled to expose the DNA and then used in a PCR amplification containing the oligonucleotide primers d75 and d76 (SEQ ID NO: 6 and 7; 200 mg) and 0.5U of Taq polymerase.

After amplification, the reaction was extracted with an equal volume of phenol/chloroform, ethanol precipitated and digested with 10U BamHI in a final volume of 30 ul. The amplified fragment was resolved on a 1% agarose gel, eluted and ligated into BamHI-digested pAc360 to produce the transfer construct pDX119. The recombinant plasmid (2 ug) and wild-type AcNPV DNA (1 ug) were co-transfected into insect cells by calcium phosphate precipitation. Inclusion negative recombinant virus was selected by visual screening. After three rounds of plaque purification, the recombinant virus (BHC-5) was expanded and expression of recombinant protein in insect cells was assessed by SDS-PAGE, Western blot and ELISA. An abundantly expressed protein of approximately 70 kD in produced in infected cells. This protein is reactive with PT-NANBH sera by Western blot and ELISA.

A further baculovirus recombinant (BHC-7) was constructed to include JG2 sequences additional to the JG3 sequences present in BHC-5, as depicted in FIG. 1. The PT-NANBH sequences present in JG2 were amplified and cloned into the pAc360 vector as described above to produce pDX118 and the appropriate Bam HI/Sal I fragments of pDX119 and pDX118 were linked together in that order in pAc360 to produce the transfer construct pDX122.

Recombinant plasmids were identified by hybridisation and orientation of inserted DNA determined by restriction enzyme analysis. Recombinant virus was produced as described above and the expressed protein analysed by SDS-PAGE, Western blot and ELISA. A very abundant (40% total cell protein) 95 kDa polypeptide which reacted with PT-NANBH sera was found in infected cells.

EXAMPLE 8

Purification of DX113 Polypeptide

*E. coli* strain TG1 containing the plasmid pDX113 (designated strain WDL001) was grown and induced in a 1.5 liter fermenter (model SET002, SGI, Newhaven, East Sussex, U.K.) at 37° C. for 5 hours. The cells were harvested by centrifugation at 5,000 g for 20 minutes and treated as follows.

a) Extraction.

The wet cells are resuspended (1:20, w/v) in Buffer A (50 mM Tris-HCl, 50 mM NaCl, 1 mM EDTA, 5 mM DTT, 10% (v/v) glycerol, pH8.0). Lysozyme was added at 5 mg solid per ml of suspension and the mixture left at 4° C. After 15 minutes, the mixture was sonicated (6 um peak-to-peak amplitude) on ice for a total of 3 minutes (6×30 sec bursts). DNase I was added at 4 ug per ml suspension and the mixture left for a further 30 minutes. The suspension was centrifuged for 20 minutes at 18,000 g(max) and the supernatant discarded.

The pellet was resuspended in buffer B (25 mM Hepes, 4M urea, 5 mM DTT, pH 8.0) at a ratio of 1:6 (w/v) to obtain a fine suspension. This was centrifuged at 18,000 g(max) for 20 minutes and the supernatant discarded. The pellet was resuspended in buffer C (25 mM Hepes, 8M urea, 2 mM DTT, pH 8.0) at a ratio of 1:6 (w/v); before suspension the following are added:—leupeptin (1 ug/ml), pepstatin (1 ug/ml) and E64 (1 ug/ml). The suspension was centrifuged at 18,000 g(max) for 30 minutes and the supernatant decanted and kept. The pellet was resuspended in 25 mM Hepes, 1% SDS pH 8.0.

b) Chromatography.

The supernatant from the 8M urea fraction was diluted 1:5 (v/v) in 25 mM Hepes, 8M urea, 2 mM DTT, pH 8.0 and fractionated on a 7 ml Q-Sepharose column. Proteins were eluted via a salt gradient of 0–1M NaCl. The chromatography and data manipulation were controlled by an FPLC (Pharmacia). DX113 elutes at approximately 500 mM NaCl and is virtually homogeneous by SDS Page and Western blot analysis.

EXAMPLE 9

Purification of BHC-5 Polypeptide

Sf9 cells ($2 \times 10^9$) were infected with a stock of the BHC-5 recombinant virus (moi 5). After incubation at 28° C. for 2 days the cells were harvested by centrifugation and then processed as follows.

a) Extraction.

The wet cell mass (1.2 g) was resuspended in 6 mls of buffer A (25 mM Hepes, 5 mM DTT, leupeptin 1 μg/ml, pepstatin 1 μg/ml, E64 1 μg/ml pH 8.0). The resuspended cells were placed on ice and sonicated for 3×15 seconds bursts (6 μm peak-to-peak amplitude) interspersed with 30 second rest periods. The sonicated suspension was centrifuged at 18,000 g(max) for 20 minutes and the supernatant discarded. The pellet was resuspended in buffer A plus 4M urea (6 mls) and centrifuged at 18,000 g (max) for 20 minutes. The supernatant was discarded and the pellet re-extracted with buffer A plus 8M urea (6 ml). After centrifugation at 18,000 g (max) for 30 minutes the supernatant was retained and diluted 1:6 in buffer A plus 8M urea. This extract was chromatographed on a mono-Q column equilibrated in the same buffer. The column was eluted via a salt gradient (0–1.0M NaCl) over 12 column volumes. BHC-5 eluted at approximately 0.45–0.55m NaCl and was greater than 90% pure as judged by SDS-PAGE. The yield, was approximately 70%.

EXAMPLE 10

Performance of DX113 and BHC-5 and 7 Polypeptides in an ELISA

Microelisa plates (96 well, Nunc) were directly coated in 50 mm bicarbonate buffer (50 mM sodium bicarbonate and 50 mM sodium carbonate, titrated to pH 9.5) with either a crude 6M urea lysate of BHC-5 or with purified pDX113. Plates were blocked with 0.2% BSA and then incubated for 30 minutes at 37° C. with sera diluted 1:20 (baculo) or 1:100 (*E. coli*). After washing in Tween-saline (0.85% saline, 0.05% Tween 20, 0.01% Bronidox) plates were incubated with peroxidase-conjugated goat anti-human immunoglobulin (1:2000) for 30 minutes at 37° C. Plates were then washed in Tween-saline and colour developed by adding the chromogenic substrate TMB (tetramethyl benzidine-HCl) (100 μl/well) and incubating for 20 minutes at room temperature. The reaction was stopped with 50 μl 2M sulphuric acid and the OD450 determined (Table 4;)

TABLE 4

Indirect anti-human Ig format ELISA for the detection of NANB antibody

|  | Baculo BHC-5 (Solid phase) | E.coli DX113 (Solid phase) |
|---|---|---|
|  | >2 | 1.670 |
|  | 1.855 | 1.531 |
|  | 1.081 | 1.015 |
| Sera from high risk | 1.842 | 1.558 |
| patients positive | 0.526 | 0.638 |
| in the assay | >2 | 1.516 |
|  | 1.823 | 1.602 |
|  | 1.779 | 1.318 |
|  | 1.122 | 0.616 |
|  | 1.686 | 1.441 |
|  | 0.259 | 0.205 |
|  | 0.158 | 0.120 |
|  | 0.298 | 0.209 |
| Sera from high risk | 0.194 | 0.111 |
| patients negative | 0.282 | 0.181 |
| in the assay | 0.263 | 0.165 |
|  | 0.184 | 0.163 |
|  | 0.121 | 0.099 |
|  | 0.243 | 0.104 |
| Accredited donor | 0.224 | 0.119 |

Sera from patients at high risk of PT-NANB infection (IVDA's, haemophiliacs) were assayed as described; all data are expressed as OD450 readings with the accredited donor as a negative control. Of this particular group of sera 10/19 are positive on both solid phases.

Additionally purified DX113 was conjugated to alkaline phosphatase using SATA/maleimide reduction and an immunometric assay was established. Known NANB positive and negative sera were diluted as indicated in accredited donor serum and added to a BHC-7 coated solid phase. Either simultaneously or after incubation (30 minutes at 37° C.) the DX113 conjugate was added (50 μl, 1:2000). After incubation at 37° C. for 30 minutes, plates were washed with 50 mM bicarbonate buffer and colour developed using the IQ Bio amplification system and the OD492 determined (Table 5)

TABLE 5

Immunometric (labelled polypeptide) ELISA for the detection of NANB antibody

| Positive in Assay | Negative in Assay | Accredited donor |
|---|---|---|
| >2 | 0.217 | 0.234 |
| 0.821 | 0.252 |  |
| >2 | 0.214 |  |
| 0.542 | 0.257 |  |
| 0.876 | 0.308 |  |
| 1.583 | 0.278 |  |
| >2 | 0.296 |  |
| >2 | 0.273 |  |
| 1.830 | 0.262 |  |
| >2 | 0.251 |  |

Thus with either assay format—antiglobulin or immunometric—all the high risk samples gave concordant results.

EXAMPLE 11

Vaccine Formulation

A vaccine formulation may be prepared by conventional techniques using the following constituents in the indicated amounts:

| | |
|---|---|
| PT-NANBH Viral polypeptide | >0.36 mg |
| Thiomersal | 0.04–0.2 mg |
| Sodium Chloride | <8.5 mg |
| Water | to 1 ml |

EXAMPLE 12

Production of Monoclonal Antibodies to PI-NANBH Polypeptides

The DNA insert from DM415 was sub-cloned into the baculovirus transfer vector p36C and recombinant virus produced by a method essentially similar to that described in Example 7. The recombinant virus was called BHC-1 and expressed very low levels of PT-NANBH-specific protein. Sf-9 cells ($5 \times 10^7$ cells/ml) infected with BHC-1 were lysed in PBS containing 1% (v/v) NP40 and spun at 13000 g for 2 minutes. The supernatant was passed over Extractigel-D (Pierce Chemicals) to remove detergent and then mixed as a 1:1 emulsion with Freund's complete adjuvant. Mice were injected subcutaneously with 0.1 ml of emulsion (equivalent to $5 \times 10^6$ cells). At 14 and 28 days post-injection, the mice were boosted by intraperitoneal injection of 0.1 ml (equivalent to $5 \times 10^6$ cells) of a detergent-free extract of BHC-5-infected Sf-9 cells: BHC-5 contains the DNA insert of DM416. Test tail bleeds were taken and assayed for anti-PT-NANBH activity in an ELISA (Example 10). Two mice with a PT-NANBH-specific response were further boosted by i.v. injection with a detergent-free extract of BHC-7-infected Sf-9 cells; BHC-7 contains a DNA insert produced by ligating together the overlapping regions of DM415 and DM416 (Example 7). The spleens were removed three days later.

Spleen cells were fused with NSo myeloma cells in the presence of PEG1500 by standard techniques. The resulting hybridoma cells were selected by growth in HAT (hypoxanthine, aminopterin, thymidine) medium. At 10–14 days post-fusion, supernatants were screened for anti-PT-NANBH activity by ELISA. Wells which showed reactivity with both DX113 and BHC-7 antigens (Example 10) were identified and individual colonies were transferred to separate wells, grown and re-tested. Wells which showed specific reactivity at this stage were further cloned at limiting dilution to ensure monoclonality.

EXAMPLE 13

Detection of PT-NANBH Viral Nucleic Acid in Seropositive Patients

Sera: Donation samples from 1400 donors, enrolled into a prospective study of post-transfusion hepatitis, were frozen at −20° C. Pre-transfusion and serial post-transfusion samples from the 260 recipients were similarly stored. The post-transfusion samples were collected fortnightly until 3 months, monthly until 6 months and 6 monthly thereafter, until 18 months. Frozen donor and recipient sera from three incidents of PT-NANBH that occurred in 1981 were also available for study. The diagnosis of PT-NANBH was based on a rise in serum alanine amino transferase (ALT) to exceed 2.5 times the upper limit of normal in at least two separate post-transfusion samples. Other hepatotropic viruses were excluded by serological testing and non-viral causes of hepatocellular injury were excluded by conventional clinical and laboratory studies.

Immunoassay: Serum samples were tested retrospectively for the presence of antibodies to HCV (C100 antigen) with the Ortho Diagnostics ELISA kit used in accordance with the manufacturer's instructions. Repeatedly reactive sera were titrated to end points in a human serum negative for anti-C100.

Detection of PT-NANBH Viral Sequences: Serum or plasma RNA was extracted, reverse transcribed, and amplified as described below. The reverse transcription/PCR oligonucleotide primers were derived from the nucleotide sequence of the JG2 clone isolated in EXAMPLE 3, and synthesised on an Applied Biosystems 381A synthesiser. The sequences of the four oligonucleotide primers were as follows:

| Designation | SEQ ID NO: | Product Size |
|---|---|---|
| d94 sense | 8 | 729 bp |
| d95 antisense | 9 | |
| N1 sense | 10 | 402 bp |
| N2 antisense | 11 | |

(i) RNA Extraction

5–50 μl of serum (or plasma) was made up to 200 μl by adding sterile distilled water. The 200 μl sample was added to an equal volume of 2×PK buffer (2×PK=0.2M TrisCl, pH7.5, 25 mM EDTA, 0.3M NaCl, 2% w/v SDS, proteinase K 200 μg/ml), mixed and incubated at 37° C. for 40 minutes. Proteins were removed by extracting twice with phenol/chloroform and once with chloroform alone. 20 μg glycogen were added to the aqueous phase and the RNA then precipitated by addition of 3 volumes of ice-cold absolute ethanol. After storage at −70° C. for 1 hour the RNA was pelleted in an Eppendorf centrifuge (15 minutes, 14000 rpm, 4° C.). The pellet was washed once in 95% ethanol, vacuum desiccated and dissolved in 10 μl of sterile distilled water. RNA solutions were stored at −70° C.

(ii) cDNA Synthesis

A 10 μl mixture was prepared containing 2 μl of the RNA solution, 50 ng of the synthetic oligonucleotide d95, 10 mM Hepes-HCl pH6.9 and 0.2 mM EDTA pH8.0. This 10 μl mix was overlayed with 2 drops of mineral oil, heated for 2 minutes in a water bath at 90° C. and cooled rapidly on ice. cDNA synthesis was performed after adjusting the reaction to contain 50 mM Tris-HCl pH7.5, 75 mM KCl, 3 mM MgCl$_2$, 10 mM DTT, 0.5 mM each of dATP, dCTP, dGTP and dTTP, 20 units of RNase inhibitor (Pharmacia) and 15 units of cloned MLV reverse transcriptase (Pharmacia) in a final volume of 20 μl. The 20 μl mix was incubated at 37° C. for 90 minutes. Following synthesis the cDNA was stored at −20° C.

(iii) "Nested" PCR

Throughout this study false positive PCR results were avoided by strict application of the contamination avoidance measures of Kwok and Higuchi (*Nature*, 1989, 339, 237–238).

a) Round 1

The polymerase chain reaction was performed in a 50 μl mix containing 10 mM Tris-HCl pH8.3, 50 mM KCl, 1.5 mM MgCl$_2$, 0.01% w/v gelatin, 1 Unit Recombinant Taq DNA polymerase (Perkin Elmer Cetus), 200 μM each DNTP, 30 ng of each 'outer' primer (d94 and d95; SEQ ID NO: 8 and 9 respectively) and 5 μl of the cDNA solution. After an initial 5 minute denaturation at 94° C., 35 cycles of 95° C. for 1.2 minutes, 56° C. for 1 minute, 72° C. for 1 minute were carried out, followed by a final 7 minute extension at 72° C. (Techne PHC-1 Automated Thermal Cycler).

b) Round 2

The reaction mix was as described above for Round 1 but 125 ng of each 'inner' primer, N1 and N2 (SEQ ID NO: 10 and 11 respectively), was used instead of the 'outer' primers d94 and d95. A 1 μl aliquot of the Round 1 PCR products was transferred to the Round 2 50 μl reaction mix. 25 cycles of 95° C. for 1.2 minutes, 46° C. for 1 minute, 72° C. for 1 minute were performed followed by a 7 minute extension at 72° C.

c) Analysis

20 μl of the Round 1 and Round 2 PCR products were analysed by electrophoresis on a 2% agarose gel. Bands were visualised by ethidium bromide staining and photographed at 302 nm.

Predictive Value of Anti-HCV Serology and PCR in the Prospective Study: Six of the 1400 donors (0.43%) enrolled into the prospective study were found to have antibodies to C100 in their serum. Of these six antibody positive donors only one (donor D6) proved to be infectious as judged by the development of PT-NANBH and C100 seroconversion in a recipient (recipient R6)—see Table 6 below.

Viral sequences were detected by PCR in the serum of donor D6 but not in any of the other five seropositive donor sera. The recipient R6 who developed PT-NANBH had also received blood from seven other donors (D7 to D13). Sera from these donors were tested and found to be both antibody negative and PCR negative.

TABLE 6

DONOR/RECIPIENT DATA SUMMARY:PROSPECTIVE STUDY

| DONORS | | | RECIPIENTS | | |
|---|---|---|---|---|---|
| Donor | anti-HCV | PCR | Recipient | PT-NANBH | Anti-HCV seroconversion |
| D1 | + | − | R1 | No | No |
| D2 | + | − | R2 | No | No |
| D3 | + | − | R3 | No | No |
| D4 | + | − | R4 | No | No |
| D5 | + | − | R5 | No | No |
| D6 | + | + | R6 | Yes* | Yes+ |
| D7 | − | − | | | |
| D8 | − | − | | | |
| D9 | − | − | | | |
| D10 | − | − | | | |
| D11 | − | − | | | |
| D12 | − | − | | | |
| D13 | − | − | | | |

*incubation period 1 month
+Seroconversion occurred at 5 months post-transfusion

EXAMPLE 14

Isolation and Expression of Additional PT-NANBH DNA Sequences

The lambda gt11 libraries prepared in Example 2 were also screened with sera from patients with a high risk for PT-NANBH but which did not react with the viral antigens, DX113, BHC-5 and BHC-7, the reasoning being that they might well contain antibodies which recognise different antigens. The sera, PJ-5 (The Newcastle Royal Infirmary, Newcastle), Birm-64 (Queen Elizabeth Medical Centre, Birmingham), PG and Le (University College and Middlesex School of Medicine, London) met this criterion and were used to screen the libraries following the same procedure as described in Examples 3 and 4. A number of recombinants were thus identified, none of which cross-hybridised with probes made from JG2 and JG3. One of the recombinants, BR11, identified by reaction with PJ-5, was selected for further analysis.

The clone, BR11, contained an insert of approximately 900 bp which was amplified by PCR using the d75 and d76 primers [SEQ ID NO: 6 and 7) as described in Example 7. The amplified sequence was directly cloned into the baculovirus vector pAc360 to form pDX128 containing an open reading frame in phase with the first 11 amino acids of polyhedrin. Recombinant baculovirus stocks (designated BHC-9) were produced following the procedure described in Example 7. Insect cells were infected with purified recombinant virus and a polypeptide of approximately 22 kD was obtained in radiolabelled cell extracts.

The amplified insert of BR11 was also cloned into pUC13 and M13 phage vector for sequencing; the DNA and aminoacid sequence data are presented in SEQ ID NO: 5. The insert contains 834 bp plus the EcoRI linkers added during cloning.

EXAMPLE 15

Performance of BHC-9 Polypeptide in an ELISA

An ELISA was established using microtitre wells coated with BHC-9-infect cell extract and an anti-human Ig conjugate detection system following the procedure as described in Example 10. A panel of high-risk sera were assayed in parallel against BHC-7 and BHC-9 and were also examined by PCR using the procedure described in Example 13. The results are shown in Table 7 in which positive samples are underlined.

TABLE 6

| Number | PCR | BHC-7 | BHC-9 |
|---|---|---|---|
| 1 | + | 2.09 | 2.00 |
| 2 | + | 2.09 | 2.00 |
| 3 | + | 1.89 | 1.37 |
| 4 | + | 1.57 | 0.27 |
| 5 | + | 1.26 | 2.00 |
| 6 | + | 0.91 | 2.00 |
| 7 | − | 0.90 | 0.51 |
| 8 | + | 0.84 | 1.19 |
| 9 | − | 0.53 | 0.43 |
| 10 | − | 0.45 | 2.00 |
| 11 | + | 0.37 | 1.07 |
| 12 | − | 0.32 | 2.00 |
| 13 | − | 0.23 | 0.30 |
| 14 | − | 0.15 | 0.43 |
| 15 | + | 0.16 | 0.76 |

TABLE 6-continued

| Number | PCR | BHC-7 | BHC-9 |
|---|---|---|---|
| 16 | – | 0.09 | 1.74 |
| 17 | – | 0.27 | 2.00 |
| 18 | – | 0.15 | 2.00 |
| 19 | – | 0.12 | 2.00 |
| 20 | – | 0.08 | 0.05 |
| cut-off |  | 0.27 | 0.29 |

Of these 20 samples, 50% are clearly positive with BHC-7 whereas 85% are positive with BHC-9. Two samples (11 & 12) which are borderline positive with BHC-7 are clearly positive with BHC-9 and some of the samples at or below the cut off with BHC-7 are positive with BHC-9. In addition, two samples (11 & 15) which were borderline or negative with BHC-7 but positive with BHC-9 are PCR-positive.

Overall there are only two samples (13 & 20) which are negative with both polypeptides and PCR.

EXAMPLE 16

Isolation of PT-NANBH DNA Sequences Overlapping Existing Clones

The immunological screening of cDNA expression libraries described in Examples 3,4 and 14, can only identify those clones which contain an immunoreactive region of the virus. Another approach to the production of clones specific for PT-NANBH is to use PCR to amplify cDNA molecules which overlap the existing clones. Sets of primers can be prepared where one member of the pair lies within existing cloned sequences and the other lies outside; this approach can be extended to nested pairs of primers as well.

cDNA, prepared as described in Example 1, was amplified by PCR, with either single or nested pairs of primers, using the reaction conditions described in Example 13. The approach is illustrated by use of the following pairs of primers; d164 (SEQ ID NO: 12) and d137 (SEQ ID NO: 13); d136 (SEQ ID NO: 14) and d155 (SEQ ID NO: 15); d156 (SEQ ID NO: 16) and d92 (SEQ ID NO 17). One member of each pair is designed to prime within existing cloned sequences (d137 and d136 prime within the 5' and 3' ends of BR11 respectively, d92 primes at the 5' end of JG3). The other primers are based upon sequences available for other PT-NANBH agents. Primer d164 corresponds to bases 10 to 31 of FIG. 2 in Okamoto et al, Japan, *J. Exp. Med.,* 1990, 60 167–177. Primers d155 and d156 correspond to positions 462 to 489 and 3315 to 3337 respectively in FIG. 47 of European Patent Application 88310922.5. One or more nucleotide substitutions were made to introduce an EcoR1 recognition site near the 5' end of the primers, except for d164 where a Bgl2 recognition site was introduced; these changes facilitate the subsequent cloning of the amplified product.

The PCR products were digested with the appropriate restriction enzyme(s), resolved by agarose gel electrophoresis and bands of the expected size were excised and cloned into both plasmid and bacteriophage vectors as described in Example 5. The sequences of the amplified DNAs 164/137 (SEQ ID NO 18), 136/155 (SEQ ID NO: 19) and 156/92 (SEQ ID NO: 20) are presented in the Sequence Listing. These new sequences extend the coverage of the PT-NANBH genome over that obtained by immunoscreening (SEQ ID NO: 3, 4 & 5). These sequences, together with others which lie within the regions already described, can be combined into a contiguous sequence at the 5' end (SEQ ID NO 21) and at the 3'-end (SEQ ID NO 22) of the PT-NANBH genome.

EXAMPLE 17

Fusion of Different PT-NANBH Antigens into a Single Recombinant Polypeptide

The data presented in Table 7 indicate that whilst more serum samples are detected as antibody-positive using BHC-9 as a target antigen (17/20) rather than BHC-7 (10/20) there are some samples (e.g. #4) which are positive with only BHC-7. This picture is borne out by wider testing of samples. Accordingly, a fusion construct was derived using sequence from BHC-7 and BHC-9.

Figure 2:
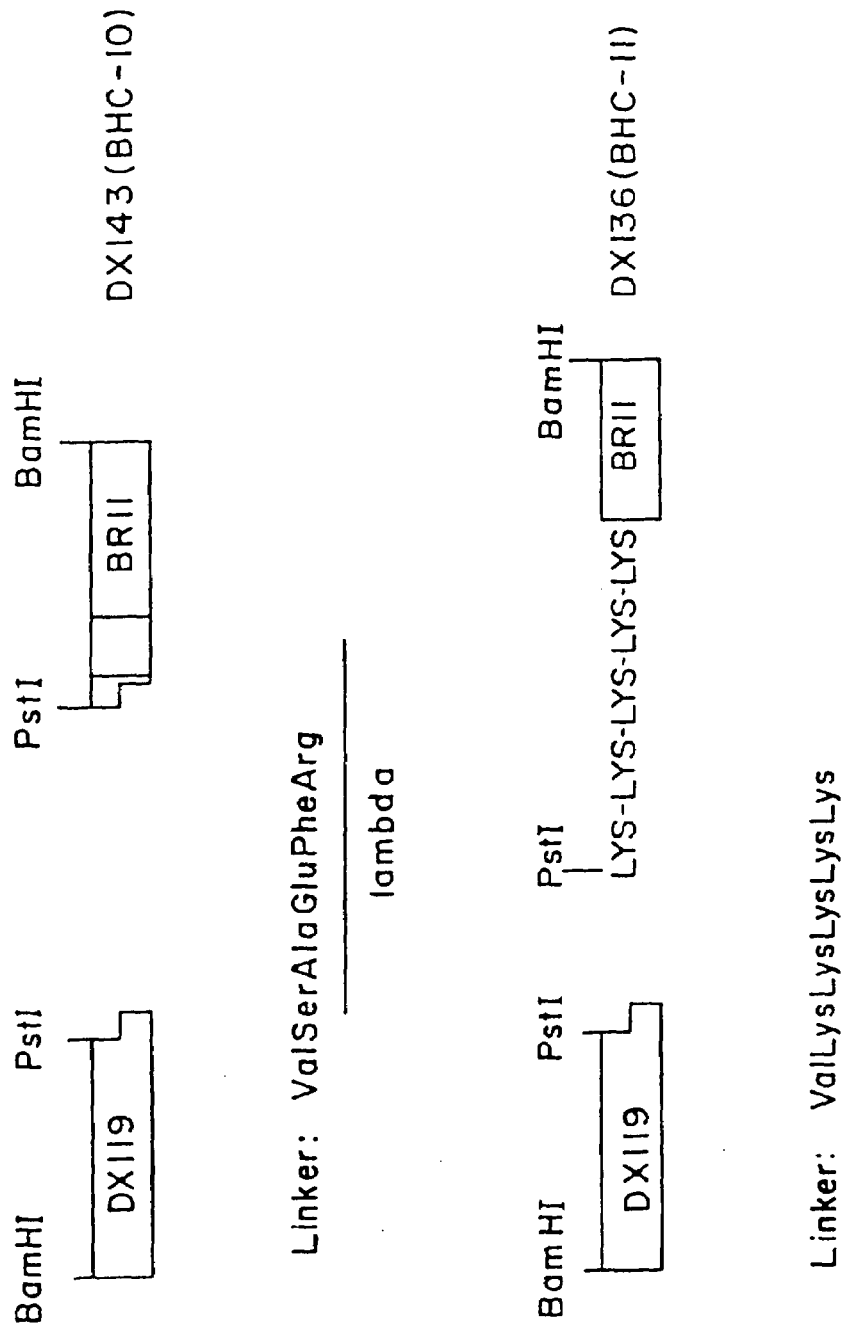

Sequences from BHC-7 and BHC-9 may be combined in a variety of ways; either sequence may be positioned at the amino terminus of the resulting fusion and the nature of the linking sequence may also be varied. FIG. 2 illustrates two possible ways in which the sequences may be combined.

Appropriate restriction fragments carrying suitable restriction enzyme sites and linker sequences were generated either by PCR using specific primers or by restriction enzyme digestion of existing plasmids. The transfer vector DX143 consists of a BamH1/Pst1 fragment from DX122 (FIG. 1; the Pst site is at position 1504 JG2, SEQ ID NO:3) linked to the 5' end of the entire coding region of BR11 (SEQ ID NO:7) which has been amplified as a Pst1/BamH1 fragment using primers d24 (SEQ ID NO:23) and d126 (SEQ ID NO:24); the linkage region consists of six amino acids derived from the d126 primer and residual bacteriophage lambda sequences. The transfer vector DX136 differs from DX143 in that the BR11 fragment was generated using d24 (SEQ ID NO: 23) and d132 (SEQ ID NO: 25) and so the linkage region contains five lysines. These transfer vectors were used to co-transfect Sf9 insect cells in culture with AcNPV DNA and plaque purified stocks of recombinant baculoviruses were produced as described in Example 7. BHC-10 was produced as a result of transfection with DX143; BHC-11 as a result of transfection with DX136.

The recombinant polypeptides expressed by these two viruses were analysed by SDS-PAGE and western blotting. BHC-10 produced a polypeptide with an apparent molecular weight of 118 kDa. BHC-11 produced a polypeptide with an apparent molecular weight of 96 kDa. Both polypeptides reacted with sera known to react in ELISA only with BHC-7 (e.g. serum A) or only with BHC-9 (serum B64, Example 14). The two polypeptides only differ in the linker sequence and this may affect either their mobility on SDS-PAGE or how they are processed in the infected cells.

EXAMPLE 18

Performance of PT-NANBH Fusion Antigens in an ELISA

An ELISA was established using microtitre wells coated with BHC-9-infected cell extracts and an anti-human Ig conjugate following the procedure described in Example 10. Table 8 presents the data from a comparison of the two fusions with the other PT-NANBH recombinant antigens BHC-7 and BHC-9 as well as the HCV recombinant protein C-100-3 (Ortho Diagnostic Systems, Raritan, N.J.). The sera are grouped by pattern of reaction with BHC-7, BHC-9 and C-100-3. Group I sera react strongly with all three antigens; Group II react strongly with only BHC-7; Group III react strongly with only BHC-9 and Group IV react strongly with only two out of the three antigens.

TABLE 8

| SERUM | BHC-7 | BHC-9 | C-100-3 | BHC-10 | BHC-11 |
|---|---|---|---|---|---|
| Group I | | | | | |
| AH | >2.0 | >2.0 | >2.0 | >2.0 | >2.0 |
| AC | >2.0 | >2.0 | >2.0 | >2.0 | >2.0 |
| 57 | >2.0 | >2.0 | >2.0 | >2.0 | >2.0 |
| 77 | >2.0 | >2.0 | >2.0 | >2.0 | >2.0 |
| 84 | 1.4 | >2.0 | >2.0 | >2.0 | >2.0 |
| Group II | | | | | |
| 805-6 | >2.0 | 0.261 | 0.1 | 1.78 | +* |
| 805-17 | >2.0 | 0.181 | 0.12 | 1.37 | +* |
| 805-149 | >2.0 | 0.651 | 0.084 | 1.57 | ++* |
| Group III | | | | | |
| JS | 0.32 | >2.0 | 0.17 | >2.0 | >2.0 |
| 805-57 | 0.069 | 1.403 | 0.25 | 1.9 | +* |
| 805-82 | 0.116 | 1.272 | 0.4 | 1.85 | ++* |
| 805-94 | 0.353 | 1.675 | 0.2 | >2.0 | +* |
| PJ1 | 0.27 | >2.0 | 0.2 | >2.0 | 1.85 |
| Group IV | | | | | |
| A | >2.0 | 0.14 | >2.0 | >2.0 | >2.0 |
| KT | 1.57 | 0.27 | >2.0 | >2.0 | >2.0 |
| Le | 0.152 | >2.0 | >2.0 | >2.0 | >2.0 |
| PJ5 | 0.123 | >2.0 | >2.0 | >2.0 | >2.0 |
| 303-923 | >2.0 | 0.9 | 0.37 | 1.9 | +* |
| 303-939 | >2.0 | 1.55 | 0.268 | 2.0 | +* |

*These samples have only been tested by western blotting on BHC-11.

These data show that both BHC-10 and BHC-11 have a similar reactivity with these sera and, most importantly, that the both antigenic activities appear to have been retained by the fusions. All the sera in Groups II & III, which react with only BHC-7 or BHC-9 respectively, give a clear reaction with the fusions. Additionally there is an indication that having the two antigens together gives a more sensitive assay. For example the sample KT gives ODs of 1.57 and 0.27 with BHC-7 and BHC-9 respectively whereas with the fusions the OD is >2.0.

What is claimed is:

1. An isolates nucleic acid encoding a polypeptide comprising an antigen, which antigen has an amino acid sequence that shares at least 90% sequence homology with the amino acid sequence encoded by the nucleotide sequence of SEQ ID NO:3, SEQ ID NO:4, SEQ ID NO:19, SEQ ID NO:20, or bases 308–2116 of the nucleotide sequence of SEQ ID NO:21, or by the nucleotide sequence of SEQ ID NO:22, wherein said antigen binds to an antibody against a post-transfusional non-A non-B hepatitis (PT-NANBH) virus.

2. The isolated nucleic acid according to claim 1, wherein said amino acid sequence shares at least 90% sequence homology with the amino acid sequence encoded by the nucleotide sequence of SEQ ID NO:3 or SEQ ID NO:4.

3. The isolated nucleic acid according to claim 2, wherein said amino acid sequence shares at least 95% sequence homology with the amino acid sequence encoded by the nucleotide sequence of SEQ ID NO:3 or SEQ ID NO:4.

4. The isolated nucleic acid according to claim 3 wherein said amino acid sequence shares at least 98% sequence homology with the amino acid sequence encoded by the nucleotide sequence of SEQ ID NO:3 or SEQ ID NO:4.

5. The isolated nucleic acid according to claim 1 wherein said amino acid sequence shares at least 95% sequence homology with the amino acid sequence encoded by the nucleotide sequence set forth in SEQ ID NO:3, SEQ ID NO:4, SEQ ID NO:19, SEQ ID NO:20 or bases 308–2116 of the nucleotide sequence of SEQ ID NO:21 or by the nucleotide sequence of SEQ ID NO:22.

6. The isolated nucleic acid according to claim 5, wherein said amino acid sequence shares at least 98% sequence homology with the amino acid sequence encoded by the nucleotide sequence of SEQ ID NO:3, SEQ ID NO:4, SEQ ID NO:19, SEQ ID NO:20 or bases 308–2116 of the nucleotide sequence of SEQ ID NO:21 or by the nucleotide sequence of SEQ ID NO:22.

7. An isolated nucleic acid encoding a polypeptide having the amino acid sequence encoded by the nucleotide sequence of SEQ ID NO:3, SEQ ID NO:4, SEQ ID NO:5, or bases 308–504 of the nucleotide sequence of SEQ ID NO:18, or by the nucleotide sequence of SEQ ID NO:19 or SEQ ID NO:20, or bases 308–2116 of the nucleotide sequence of SEQ ID NO:21 or by the nucleotide sequence of SEQ ID NO:22.

8. The isolated nucleic acid according to claim 7, wherein said polypeptide has the amino acid sequence encoded by the nucleotide sequence of SEQ ID NO:3, SEQ ID NO:4, or SEQ ID NO:5.

9. The isolated nucleic acid according to claim 8 wherein said polypeptide has the amino acid sequence encoded by the nucleotide sequence of SEQ ID NO:3 or SEQ ID NO:4.

10. An isolated nucleic acid encoding a polypeptide comprising an antigen having an amino acid sequence that shares at least 98% sequence homology with the amino acid sequence encoded by the nucleotide sequence by SEQ ID NO:5.

11. An isolated nucleic acid encoding a polypeptide comprising an antigen having an amino acid sequence that shares at least 98% sequence homology with the amino acid sequence encoded by the nucleotide sequence of SEQ ID NO:18 from bases 308–504.

12. An isolated nucleic acid having the nucleotide sequence of SEQ ID NO:3, SEQ ID NO:4, SEQ ID NO:5, bases 308–504 of the nucleotide sequence of SEQ NO:18, SEQ ID NO:19, SEQ ID NO:20, bases 308–2116 of the nucleotide sequence of SEQ ID NO:21 or the nucleotide sequence of SEQ ID NO:22.

13. The isolated nucleic acid according to any one of claims 1, 7, 10, 11, and 12 wherein said nucleic acid is DNA.

14. An expression vector comprising the nucleic acid of any one of claims 1, 7, 10, 11 and 12.

15. A host cell comprising the expression vector of claim 14.

16. A process for preparing a polypeptide comprising culturing the host cell according to claim 15 under conditions so that said nucleic acid is expressed and said polypeptide is thereby produced.

\* \* \* \* \*

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 21 bases
      (B) TYPE: nucleotide
      (C) STRANDEDNESS: single
      (D) TOPOLOGY: linear (ii) MOLECULE TYPE: synthetic DNA (vi) ORIGINAL SOURCE:
      (A) ORGANISM: bacteriophage lambda gt11

(vii) IMMEDIATE SOURCE:
      (A) LIBRARY: Oligonucleotide synthesizer; oligo d19

(ix) FEATURE:
      (B) LOCATION: from 1 to 21 bases homologous to upstream
         portion of lacZ gene flanking the EcoR1 site in
         bacteriophage lambda gt11
      (D) OTHER INFORMATION: primes DNA synthesis from the phage
         vector into cDNA inserted at the EcoR1 site.

(xi) SEQUENCE DESCRIPTION: SEQ ID NO:1:

GGTGGCGACG ACTCCTGGAG C                    21

(2) INFORMATION FOR SEQ ID NO:2:

(i) SEQUENCE CHARACTERISTICS:
      (A) LENGTH: 21 bases
      (B) TYPE: nucleotide

```
            (C) STRANDEDNESS: single
            (D) TOPOLOGY: linear (ii) MOLECULE TYPE: synthetic DNA (vi) ORIGINAL SOURCE:
            (A) ORGANISM: bacteriophage lambda gt11

(vii) IMMEDIATE SOURCE:
            (A) LIBRARY: Oligonucleotide synthesizer; oligo d20

(ix) FEATURE:
            (B) LOCATION: from 1 to 21 bases homologous to downstream
                portion of lacZ gene flanking the EcoR1 site in
                bacteriophage lambda gt11
            (D) OTHER INFORMATION: primes DNA synthesis from the phage
                vector into cDNA inserted at the EcoR1
                site.

(xi) SEQUENCE DESCRIPTION: SEQ ID NO:2:

TTGACACCAG ACCAACTGGT A                                              21

(2) INFORMATION FOR SEQ ID NO:3:

(i) SEQUENCE CHARACTERISTICS:
            (A) LENGTH: 1770 base pairs
            (B) TYPE: nucleotide with corresponding protein
            (C) STRANDEDNESS: single
            (D) TOPOLOGY: linear (ii) MOLECULE TYPE: cDNA to genomic RNA (vi) ORIGINAL SOURCE:
            (A) ORGANISM: human; serum infectious for PT-NANBH (vii) IMMEDIATE SOURCE:
            (A) LIBRARY: clone JG2 from cDNA library in lambda gt11

(ix) FEATURE:
            (B) LOCATION: from 1 to 1770 bp portion of the PT-NANBH
                polyprotein
            (D) OTHER INFORMATION: probably encodes viral non-structural
                proteins (xi) SEQUENCE DESCRIPTION: SEQ ID NO:3:

CAA AAT GAC TTC CCA GAC GCT GAC CTC ATC GAG GCC AAC CTC CTG TGG       48
Gln Asn Asp Phe Pro Asp Ala Asp Leu Ile Glu Ala Asn Leu Leu Trp
                 5                  10                  15

CGG CAT GAG ATG GGC GGG GAC ATT ACC CGC GTG GAG TCA GAG AAC AAG       96
Arg His Glu Met Gly Gly Asp Ile Thr Arg Val Glu Ser Glu Asn Lys
             20                  25                  30

GTA GTA ATC CTG GAC TCT TTC GAC CCG CTC CGA GCG GAG GAG GAT GAG      144
Val Val Ile Leu Asp Ser Phe Asp Pro Leu Arg Ala Glu Glu Asp Glu
         35                  40                  45

CGG GAA GTG TCC GTC CCG GCG GAG ATC CTG CGG AAA TCC AAG AAA TTC      192
Arg Glu Val Ser Val Pro Ala Glu Ile Leu Arg Lys Ser Lys Lys Phe
     50                  55                  60

CCA CCA GCG ATG CCC GCA TGG GCA CGC CCG GAT TAC AAC CCT CCG CTG      240
Pro Pro Ala Met Pro Ala Trp Ala Arg Pro Asp Tyr Asn Pro Pro Leu
 65                  70                  75                  80

CTG GAG TCC TGG AAG GCC CCG GAC TAC GTC CCT CCA GTG GTA CAT GGG      288
Leu Glu Ser Trp Lys Ala Pro Asp Tyr Val Pro Pro Val Val His Gly
                 85                  90                  95

TGC CCA CTG CCA CCT ACT AAG ACC CCT CCT ATA CCA CCT CCA CGG AGA      336
Cys Pro Leu Pro Pro Thr Lys Thr Pro Pro Ile Pro Pro Pro Arg Arg
            100                 105                 110

AAG AGG ACA GTT GTT CTG ACA GAA TCC ACC GTG TCT TCT GCC CTG GCG      384
Lys Arg Thr Val Val Leu Thr Glu Ser Thr Val Ser Ser Ala Leu Ala
        115                 120                 125
```

-continued

| | |
|---|---|
| GAG CTT GCC ACA AAG GCT TTT GGT AGC TCC GGA CCG TCG GCC GTC GAC<br>Glu Leu Ala Thr Lys Ala Phe Gly Ser Ser Gly Pro Ser Ala Val Asp<br>130                         135                       140 | 432 |
| AGC GGC ACG GCA ACC GCC CCT CCT GAC CAA TCC TCC GAC GAC GGC GGA<br>Ser Gly Thr Ala Thr Ala Pro Pro Asp Gln Ser Ser Asp Asp Gly Gly<br>145                     150                      155                    160 | 480 |
| GCA GGA TCT GAC GTT GAG TCG TAT TCC TCC ATG CCC CCC CTT GAG GGG<br>Ala Gly Ser Asp Val Glu Ser Tyr Ser Ser Met Pro Pro Leu Glu Gly<br>                   165                      170                    175 | 528 |
| GAG CCG GGG GAC CCC GAT CTC AGC GAC GGG TCT TGG TCT ACC GTG AGT<br>Glu Pro Gly Asp Pro Asp Leu Ser Asp Gly Ser Trp Ser Thr Val Ser<br>          180                      185                    190 | 576 |
| GAG GAG GCC GGT GAG GAC GTC GTC TGC TGC TCG ATG TCC TAC ACA TGG<br>Glu Glu Ala Gly Glu Asp Val Val Cys Cys Ser Met Ser Tyr Thr Trp<br>195                     200                      205 | 624 |
| ACA GGC GCT CTG ATC ACG CCA TGC GCT GCG GAG GAA AGC AAG CTG CCC<br>Thr Gly Ala Leu Ile Thr Pro Cys Ala Ala Glu Glu Ser Lys Leu Pro<br>          210                      215                    220 | 672 |
| ATC AAC GCG TTG AGC AAC TCT TTG CTG CGT CAC CAC AAC ATG GTC TAC<br>Ile Asn Ala Leu Ser Asn Ser Leu Leu Arg His His Asn Met Val Tyr<br>225                     230                      235                    240 | 720 |
| GCT ACC ACA TCC CGC AGC GCA AGC CAG CGG CAG AAG AAG GTC ACC TTT<br>Ala Thr Thr Ser Arg Ser Ala Ser Gln Arg Gln Lys Lys Val Thr Phe<br>                   245                      250                    255 | 768 |
| GAC AGA CTG CAA ATC CTG GAC GAT CAC TAC CAG GAC GTG CTC AAG GAG<br>Asp Arg Leu Gln Ile Leu Asp Asp His Tyr Gln Asp Val Leu Lys Glu<br>          260                      265                    270 | 816 |
| ATG AAG GCG AAG GCG TCC ACA GTT AAG GCT AAG CTT CTA TCA GTA GAG<br>Met Lys Ala Lys Ala Ser Thr Val Lys Ala Lys Leu Leu Ser Val Glu<br>275                     280                      285 | 864 |
| GAA GCC TGC AAG CTG ACG CCC CCA CAT TCG GCC AAA TCT AAA TTT GGC<br>Glu Ala Cys Lys Leu Thr Pro Pro His Ser Ala Lys Ser Lys Phe Gly<br>          290                      295                    300 | 912 |
| TAT GGG GCA AAG GAC GTC CGG AAC CTA TCC AGC AAG GCC ATT AAC CAC<br>Tyr Gly Ala Lys Asp Val Arg Asn Leu Ser Ser Lys Ala Ile Asn His<br>305                     310                      315                    320 | 960 |
| ATC CGC TCC GTG TGG GAG GAC TTG TTG GAA GAC ACT GAA ACA CCA ATT<br>Ile Arg Ser Val Trp Glu Asp Leu Leu Glu Asp Thr Glu Thr Pro Ile<br>                   325                      330                    335 | 1008 |
| GAC ACC ACC ATC ATG GCA AAA AAT GAG GTT TTC TGC GTC CAA CCA GAG<br>Asp Thr Thr Ile Met Ala Lys Asn Glu Val Phe Cys Val Gln Pro Glu<br>          340                      345                    350 | 1056 |
| AGA GGA GGC CGC AAG CCA GCT CGC CTT ATC GTG TTC CCA GAC TTG GGG<br>Arg Gly Gly Arg Lys Pro Ala Arg Leu Ile Val Phe Pro Asp Leu Gly<br>355                     360                      365 | 1104 |
| GTC CGT GTG TGC GAG AAA ATG GCC CTC TAT GAC GTG GTC TCC ACC CTC<br>Val Arg Val Cys Glu Lys Met Ala Leu Tyr Asp Val Val Ser Thr Leu<br>          370                      375                    380 | 1152 |
| CCT CAG GCT GTG ATG GGC TCC TCG TAC GGA TTC CAG TAT TCT CCT GGA<br>Pro Gln Ala Val Met Gly Ser Ser Tyr Gly Phe Gln Tyr Ser Pro Gly<br>385                     390                      395                    400 | 1200 |
| CAG CGG GTC GAG TTC CTG GTG AAC GCC TGG AAA TCA AAG AAG ACC CCT<br>Gln Arg Val Glu Phe Leu Val Asn Ala Trp Lys Ser Lys Lys Thr Pro<br>                   405                      410                    415 | 1248 |
| ATG GGC TTT GCA TAT GAC ACC CGC TGT TTT GAC TCA ACA GTC ACT GAG<br>Met Gly Phe Ala Tyr Asp Thr Arg Cys Phe Asp Ser Thr Val Thr Glu<br>          420                      425                    430 | 1296 |
| AAT GAC ATC CGT GTA GAG GAG TCA ATT TAT CAA TGT TGT GAC TTG GCC<br>Asn Asp Ile Arg Val Glu Glu Ser Ile Tyr Gln Cys Cys Asp Leu Ala | 1344 |

```
                435                 440                 445
CCC GAA GCC AGA CAG GCC ATA AGG TCG CTC ACA GAG CGG CTT TAT ATC          1392
Pro Glu Ala Arg Gln Ala Ile Arg Ser Leu Thr Glu Arg Leu Tyr Ile
        450                 455                 460

GGG GGT CCC CTG ACT AAT TCA AAA GGG CAG AAC TGC GGC TAT CGC CGG          1440
Gly Gly Pro Leu Thr Asn Ser Lys Gly Gln Asn Cys Gly Tyr Arg Arg
465                 470                 475                 480

TGC CGC GCG AGC GGC GTG CTG ACG ACT AGC TGC GGT AAT ACC CTC ACA          1488
Cys Arg Ala Ser Gly Val Leu Thr Thr Ser Cys Gly Asn Thr Leu Thr
                485                 490                 495

TGT TAC TTG AAG GCC TCT GCA GCC TGT CGA GCT GCA AAG CTC CAG GAC          1536
Cys Tyr Leu Lys Ala Ser Ala Ala Cys Arg Ala Ala Lys Leu Gln Asp
            500                 505                 510

TGC ACG ATG CTC GTG TGC GGA GAC GGC CTT GTC GTT ATC TGT GAG AGC          1584
Cys Thr Met Leu Val Cys Gly Asp Gly Leu Val Val Ile Cys Glu Ser
        515                 520                 525

GCG GGA ACC CAG GAG GAC GCG GCG AGC CTA CGA GTC TTC ACG GAG GCT          1632
Ala Gly Thr Gln Glu Asp Ala Ala Ser Leu Arg Val Phe Thr Glu Ala
530                 535                 540

ATG ACT AGG TAC TCT GCC CCC CCC GGG GAC CCG CCC CAA CCA GAA TAC          1680
Met Thr Arg Tyr Ser Ala Pro Pro Gly Asp Pro Pro Gln Pro Glu Tyr
545                 550                 555                 560

GAC CTG GAG TTG ATA ACA TCA TGC TCC TCC AAT GTG TCG GTC GCG CAC          1728
Asp Leu Glu Leu Ile Thr Ser Cys Ser Ser Asn Val Ser Val Ala His
                565                 570                 575

GAT GCA TCT GGC AAA AGG GTA TAC TAC CTC ACC CGT GAC CCG                  1770
Asp Ala Ser Gly Lys Arg Val Tyr Tyr Leu Thr Arg Asp Pro
            580                 585                 590

(2) INFORMATION FOR SEQ ID NO:4:

(i) SEQUENCE CHARACTERISTICS:
        (A) LENGTH: 1035 base pairs
        (B) TYPE: nucleotide with corresponding protein
        (C) STRANDEDNESS: single
        (D) TOPOLOGY: linear (ii) MOLECULE TYPE: cDNA to genomic RNA (vi) ORIGINAL SOURCE:
        (A) ORGANISM: human; serum infectious for PT-NANBH (vii) IMMEDIATE SOURCE:
        (A) LIBRARY: clone JG3 from cDNA library in lambda gt11

(ix) FEATURE:
        (B) LOCATION: from 1 to 1035 bp portion of the PT-NANBH
            polyprotein
        (D) OTHER INFORMATION: probably encodes viral non-structural
            proteins (xi) SEQUENCE DESCRIPTION: SEQ ID NO:4:

ACA GAA GTG GAT GGG GTG CGG CTG CAC AGG TAC GCT CCG GCG TGC AAA          48
Thr Glu Val Asp Gly Val Arg Leu His Arg Tyr Ala Pro Ala Cys Lys
                5                   10                  15

CCT CTC CTA CGG GAG GAG GTC ACA TTC CAG GTC GGG CTC AAC CAA TAC          96
Pro Leu Leu Arg Glu Glu Val Thr Phe Gln Val Gly Leu Asn Gln Tyr
            20                  25                  30

CTG GTT GGG TCG CAG CTC CCA TGC GAG CCC GAA CCG GAT GTA GCA GTG          144
Leu Val Gly Ser Gln Leu Pro Cys Glu Pro Glu Pro Asp Val Ala Val
        35                  40                  45

CTC ACT TCC ATG CTC ACC GAC CCC TCC CAC ATC ACA GCA GAG ACG GCT          192
Leu Thr Ser Met Leu Thr Asp Pro Ser His Ile Thr Ala Glu Thr Ala
50                  55                  60
```

```
AAG CGC AGG CTG GCC AGG GGG TCT CCC CCC TCC TTG GCC AGC TCT TCA      240
Lys Arg Arg Leu Ala Arg Gly Ser Pro Pro Ser Leu Ala Ser Ser Ser
 65          70                  75                  80

GCT AGC CAG TTG TCT GGC CCT TCC TCG AAG GCG ACA TAC ATT ACC CAA      288
Ala Ser Gln Leu Ser Gly Pro Ser Ser Lys Ala Thr Tyr Ile Thr Gln
                 85                  90                  95

AAT GAC TTC CCA GAC GCT GAC CTC ATC GAG GCC AAC CTC CTG TGG CGG      336
Asn Asp Phe Pro Asp Ala Asp Leu Ile Glu Ala Asn Leu Leu Trp Arg
                100                 105                 110

CAT GAG ATG GGC GGG GAC ATT ACC CGC GTG GAG TCA GAG AAC AAG GTA      384
His Glu Met Gly Gly Asp Ile Thr Arg Val Glu Ser Glu Asn Lys Val
            115                 120                 125

GTA ATC CTG GAC TCT TTC GAC CCG CTC CGA GCG GAG GAG GAT GAG CGG      432
Val Ile Leu Asp Ser Phe Asp Pro Leu Arg Ala Glu Glu Asp Glu Arg
130                 135                 140

GAA GTG TCC GTC CCG GCG GAG ATC CTG CGG AAA TCC AAG AAA TTC CCA      480
Glu Val Ser Val Pro Ala Glu Ile Leu Arg Lys Ser Lys Lys Phe Pro
145                 150                 155                 160

CCA GCG ATG CCC GCA TGG GCA CGC CCG GAT TAC AAC CCT CCG CTG CTG      528
Pro Ala Met Pro Ala Trp Ala Arg Pro Asp Tyr Asn Pro Pro Leu Leu
                165                 170                 175

GAG TCC TGG AAG GCC CCG GAC TAC GTC CCT CCA GTG GTA CAT GGG TGC      576
Glu Ser Trp Lys Ala Pro Asp Tyr Val Pro Pro Val Val His Gly Cys
            180                 185                 190

CCA CTG CCA CCT ACT AAG ACC CCT CCT ATA CCA CCT CCA CGG AGA AAG      624
Pro Leu Pro Pro Thr Lys Thr Pro Pro Ile Pro Pro Pro Arg Arg Lys
        195                 200                 205

AGG ACA GTT GTT CTG ACA GAA TCC ACC GTG TCT TCT GCC CTG GCG GAG      672
Arg Thr Val Val Leu Thr Glu Ser Thr Val Ser Ser Ala Leu Ala Glu
210                 215                 220

CTT GCC ACA AAG GCT TTT GGT AGC TCC GGA CCG TCG GCC GTC GAC AGC      720
Leu Ala Thr Lys Ala Phe Gly Ser Ser Gly Pro Ser Ala Val Asp Ser
225                 230                 235                 240

GGC ACG GCA ACC GCC CCT CCT GAC CAA TCC TCC GAC GAC GGC GGA GCA      768
Gly Thr Ala Thr Ala Pro Pro Asp Gln Ser Ser Asp Asp Gly Gly Ala
                245                 250                 255

GGA TCT GAC GTT GAG TCG TAT TCC TCC ATG CCC CCC CTT GAG GGG GAG      816
Gly Ser Asp Val Glu Ser Tyr Ser Ser Met Pro Pro Leu Glu Gly Glu
            260                 265                 270

CCG GGG GAC CCC GAT CTC AGC GAC GGG TCT TGG TCT ACC GTG AGT GAG      864
Pro Gly Asp Pro Asp Leu Ser Asp Gly Ser Trp Ser Thr Val Ser Glu
        275                 280                 285

GAG GCC GGT GAG GAC GTC GTC TGC TGC TCG ATG TCC TAC ACA TGG ACA      912
Glu Ala Gly Glu Asp Val Val Cys Cys Ser Met Ser Tyr Thr Trp Thr
290                 295                 300

GGC GCT CTG ATC ACG CCA TGC GCT GCG GAG GAA AGC AAG CTG CCC ATC      960
Gly Ala Leu Ile Thr Pro Cys Ala Ala Glu Glu Ser Lys Leu Pro Ile
305                 310                 315                 320

AAC GCG TTG AGC AAC TCT TTG CTG CGT CAC CAC AAC ATG GTC TAC GCT     1008
Asn Ala Leu Ser Asn Ser Leu Leu Arg His His Asn Met Val Tyr Ala
                325                 330                 335

ACC ACA TCC CGC AGC GCA AGC CAG CGG                                 1035
Thr Thr Ser Arg Ser Ala Ser Gln Arg
                340                 345

(2) INFORMATION FOR SEQ ID NO:5:

(i) SEQUENCE CHARACTERISTICS:
        (A) LENGTH: 834 base pairs
        (B) TYPE: nucleotide with corresponding protein
        (C) STRANDEDNESS: single
```

-continued

```
        (D) TOPOLOGY: linear (ii) MOLECULE TYPE: cDNA to genomic RNA (vi) ORIGINAL SOURCE:
        (A) ORGANISM: human; serum infectious for PT-NANBH (vii) IMMEDIATE SOURCE:
        (A) LIBRARY: clone BR11 from cDNA library in lambda gt11

(ix) FEATURE:
        (B) LOCATION: from 1 to 834 bp portion of the PT-NANBH
            polyprotein
        (D) OTHER INFORMATION: probably encodes viral structural
            proteins (xi) SEQUENCE DESCRIPTION: SEQ ID NO:5:

AGA AAA ACC AAA CGT AAC ACC AAC CTC CGC CCA CAG GAC GTC AGG TTC         48
Arg Lys Thr Lys Arg Asn Thr Asn Leu Arg Pro Gln Asp Val Arg Phe
                  5                  10                  15

CCG GGC GGT GGT CAG ATC GTT GGT GGA GTT TAC CTG TTG CCG CGC AGG         96
Pro Gly Gly Gly Gln Ile Val Gly Gly Val Tyr Leu Leu Pro Arg Arg
             20                  25                  30

GGC CCC AGG TTG GGT GTG CGC GCG ACT AGG AAG ACT TCC GAG CGG TCG        144
Gly Pro Arg Leu Gly Val Arg Ala Thr Arg Lys Thr Ser Glu Arg Ser
         35                  40                  45

CAA CCT CGT GGA AGG CGA CAA CCT ATC CCC AAG GCT CGC CAG CCC GAG        192
Gln Pro Arg Gly Arg Arg Gln Pro Ile Pro Lys Ala Arg Gln Pro Glu
     50                  55                  60

GGC AGG GCC TGG GCT CAG CCC GGG TAC CCT TGG CCC CTC TAT GGC AAC        240
Gly Arg Ala Trp Ala Gln Pro Gly Tyr Pro Trp Pro Leu Tyr Gly Asn
 65                  70                  75                  80

GAG GGC ATG GGG TGG GCA GGA TGG CTC CTG TCA CCC CGT GGC TCC CGG        288
Glu Gly Met Gly Trp Ala Gly Trp Leu Leu Ser Pro Arg Gly Ser Arg
                 85                  90                  95

CCT AGT TGG GGC CCC ACT GAC CCC CGG CGT AGG TCG CGT AAT TTG GGT        336
Pro Ser Trp Gly Pro Thr Asp Pro Arg Arg Arg Ser Arg Asn Leu Gly
            100                 105                 110

AAA GTC ATC GAT ACC CTC ACA TGC GGC TTC GCC GAC TCT CAT GGG GTA        384
Lys Val Ile Asp Thr Leu Thr Cys Gly Phe Ala Asp Ser His Gly Val
        115                 120                 125

CAT TCC GCT CGT CGG CGC TCC CTT AGG GGC GCT GCC AGG GCC CTG GCG        432
His Ser Ala Arg Arg Arg Ser Leu Arg Gly Ala Ala Arg Ala Leu Ala
    130                 135                 140

CAT GGC GTC CGG GTT CTG GAG GAC GGC GTG AAC TAT GCA ACA GGG AAT        480
His Gly Val Arg Val Leu Glu Asp Gly Val Asn Tyr Ala Thr Gly Asn
145                 150                 155                 160

TTA CCC GGT TGC TCT TTC TCT ATC TTC CTC TTG GCT TTG CTG TCC TGT        528
Leu Pro Gly Cys Ser Phe Ser Ile Phe Leu Leu Ala Leu Leu Ser Cys
                165                 170                 175

TTG ACC ATT CCA GCT TCC GCT TAT GAA GTG CGC AAC GTG TCC GGG ATC        576
Leu Thr Ile Pro Ala Ser Ala Tyr Glu Val Arg Asn Val Ser Gly Ile
            180                 185                 190

TAC CAT GTC ACG AAC GAT TGC TCC AAC TCA AGC ATC GTG TAC GAG ACA        624
Tyr His Val Thr Asn Asp Cys Ser Asn Ser Ser Ile Val Tyr Glu Thr
        195                 200                 205

GCG GAC ATG ATC ATG CAC ACC CCC GGG TGT GTG CCC TGT GTC CGG GAG        672
Ala Asp Met Ile Met His Thr Pro Gly Cys Val Pro Cys Val Arg Glu
    210                 215                 220

GGT AAT TCC TCC CGC TGC TGG GTA GCG CTC ACT CCC ACG CTC GCG GCC        720
Gly Asn Ser Ser Arg Cys Trp Val Ala Leu Thr Pro Thr Leu Ala Ala
225                 230                 235                 240

AAG GAC GCC AGC ATC CCC ACT GCG ACA ATA CGA CGC CAC GTC GAT TTG        768
```

```
            Lys Asp Ala Ser Ile Pro Thr Ala Thr Ile Arg Arg His Val Asp Leu
                        245                 250                 255

CTC GTT GGG GCG GCT GCC TTC TCG TCC GCT ATG TAC GTG GGG GAT CTC           816
Leu Val Gly Ala Ala Ala Phe Ser Ser Ala Met Tyr Val Gly Asp Leu
            260                 265                 270

TGC GGA TCT GTT TTC CCG                                                    834
Cys Gly Ser Val Phe Pro
        275
```

(2) INFORMATION FOR SEQ ID NO:6:

(i) SEQUENCE CHARACTERISTICS:
        (A) LENGTH: 31 bases
        (B) TYPE: nucleotide
        (C) STRANDEDNESS: single
        (D) TOPOLOGY: linear (ii) MOLECULE TYPE: synthetic DNA (vi) ORIGINAL SOURCE:
        (A) ORGANISM: bacteriophage lambda gt11

(vii) IMMEDIATE SOURCE:
        (A) LIBRARY: Oligonucleotide synthesizer; oligo d75

(ix) FEATURE:
        (B) LOCATION: from 4 to 9 bases BamH1 site, from 10 to 31
           bases homologous to upstream portion of lacZ gene
           flanking the EcoR1 site in bacteriophage lambda gt11 from
           26 to 31 bases EcoR1 site
        (D) OTHER INFORMATION: primes DNA synthesis from the phage
           vector into cDNA inserted at the EcoR1 site and
           introduces a BamH1 site suitable for subsequent cloning
           into expression vectors.

(xi) SEQUENCE DESCRIPTION: SEQ ID NO:6:

```
TAAGGATCCC CCGTCAGTAT CGGCGGAATT C                                         31
```

(2) INFORMATION FOR SEQ ID NO:7:

(i) SEQUENCE CHARACTERISTICS:
        (A) LENGTH: 30 bases
        (B) TYPE: nucleotide
        (C) STRANDEDNESS: single
        (D) TOPOLOGY: linear (ii) MOLECULE TYPE: synthetic DNA (vi) ORIGINAL SOURCE:
        (A) ORGANISM: bacteriophage lambda gt11

(vii) IMMEDIATE SOURCE:
        (A) LIBRARY: Oligonucleotide synthesizer; oligo d76

(ix) FEATURE:
        (B) LOCATION: from 4 to 9 bases BamH1 site from 10 to 30 bases
           homologous to downstream portion of lacZ gene flanking
           the EcoR1 site in bacteriophage lambda gt11
        (D) OTHER INFORMATION: primes DNA synthesis from the phage
           vector into cDNA inserted at the EcoR1 site and
           introduces a BamH1 site suitable for subsequent cloning
           into expression vectors.

(xi) SEQUENCE DESCRIPTION: SEQ ID NO:7:

```
TATGGATCCG TAGCGACCGG CGCTCAGCTG                                           30
```

(2) INFORMATION FOR SEQ ID NO:8:

(i) SEQUENCE CHARACTERISTICS:
        (A) LENGTH: 19 bases
        (B) TYPE: nucleotide
        (C) STRANDEDNESS: single (D) TOPOLOGY: linear (ii) MOLECULE TYPE: synthetic DNA (vi) ORIGINAL SOURCE:
        (A) ORGANISM: human; serum infectious for PT-NANBH (vii) IMMEDIATE SOURCE:
        (A) LIBRARY: oligonucleotide synthesizer; oligo d94

(ix) FEATURE:
        (B) LOCATION: from 1 to 19 bases homologous to bases 914 to
            932 of the sense strand of JG2 (SEQ ID NO:3)
        (D) OTHER INFORMATION: primes DNA synthesis on the negative
            strand of PT-NANBH genomic RNA/DNA.

(xi) SEQUENCE DESCRIPTION: SEQ ID NO:8:

ATGGGGCAAA GGACGTCCG                                                    19

(2) INFORMATION FOR SEQ ID NO:9:

(i) SEQUENCE CHARACTERISTICS:
        (A) LENGTH: 24 bases
        (B) TYPE: nucleotide
        (C) STRANDEDNESS: single
        (D) TOPOLOGY: linear (ii) MOLECULE TYPE: synthetic DNA (vi) ORIGINAL SOURCE:
        (A) ORGANISM: human; serum infectious for PT-NANBH (vii) IMMEDIATE SOURCE:
        (A) LIBRARY: oligonucleotide synthesizer; oligo d95

(ix) FEATURE:
        (B) LOCATION: from 1 to 24 bases homologous to bases 1620 to
            1643 of the anti-sense strand of JG2 (SEQ ID NO:3)
        (D) OTHER INFORMATION: primes DNA synthesis on the positive
            strand of PT-NANBH genomic RNA/DNA.

(xi) SEQUENCE DESCRIPTION: SEQ ID NO:9:

TACCTAGTCA TAGCCTCCGT GAAG                                              24

(2) INFORMATION FOR SEQ ID NO:10:

(i) SEQUENCE CHARACTERISTICS:
        (A) LENGTH: 17 bases
        (B) TYPE: nucleotide
        (C) STRANDEDNESS: single
        (D) TOPOLOGY: linear (ii) MOLECULE TYPE: synthetic DNA (vi) ORIGINAL SOURCE:
        (A) ORGANISM: human; serum infectious for PT-NANBH (vii) IMMEDIATE SOURCE:
        (A) LIBRARY: oligonucleotide synthesizer; oligo N1

(ix) FEATURE:
        (B) LOCATION: from 1 to 17 bases homologous to bases 1033 to
            1049 of the sense strand of JG2 (SEQ ID NO:3)
        (D) OTHER INFORMATION: primes DNA synthesis on the negative
            strand of PT-NANBH genomic RNA/DNA.

(xi) SEQUENCE DESCRIPTION: SEQ ID NO:10:

GAGGTTTTCT GCGTCCA                                                      17

(2) INFORMATION FOR SEQ ID NO:11:

(i) SEQUENCE CHARACTERISTICS:
        (A) LENGTH: 17 bases

```
        (B) TYPE: nucleotide
        (C) STRANDEDNESS: single
        (D) TOPOLOGY: linear (ii) MOLECULE TYPE: synthetic DNA (vi) ORIGINAL SOURCE:
        (A) ORGANISM: human; serum infectious for PT-NANBH (vii) IMMEDIATE SOURCE:
        (A) LIBRARY: oligonucleotide synthesizer; oligo N2

(ix) FEATURE:
        (B) LOCATION: from 1 to 17 bases homologous to bases 1421 to
            1437 of the anti-sense strand of JG2 (SEQ ID NO:3)
        (D) OTHER INFORMATION: primes DNA synthesis on the positive
            strand of PT-NANBH genomic RNA/DNA.

(xi) SEQUENCE DESCRIPTION: SEQ ID NO:11:

GCGATAGCCG CAGTTCT                                                    17

(2) INFORMATION FOR SEQ ID NO:12:

(i) SEQUENCE CHARACTERISTICS:
        (A) LENGTH: 22 bases
        (B) TYPE: nucleotide
        (C) STRANDEDNESS: single
        (D) TOPOLOGY: linear (ii) MOLECULE TYPE: synthetic DNA (vi) ORIGINAL SOURCE:
        (A) ORGANISM: human; serum infectious for PT-NANBH (vii) IMMEDIATE SOURCE:
        (A) LIBRARY: oligonucleotide synthesizer; oligo d164

(ix) FEATURE:
        (B) LOCATION: from 1 to 22 bases homologous to bases 10 to
            31 of the sequence in Fig. 2 of Okamoto et al., Japan. J.
            Exp. Med., 1990, 60 167-177, base 22 changed from A to T
            to introduce Bgl2 recognition site from 8 to 13 bases
            Bgl2 recognition site
        (D) OTHER INFORMATION: primes DNA synthesis on the negative
            strand of PT-NANBH genomic RNA/DNA and introduces a Bgl2
            site.

(xi) SEQUENCE DESCRIPTION: SEQ ID NO:12:

CCACCATAGA TCTCTCCCCT GT                                              22

(2) INFORMATION FOR SEQ ID NO:13:

(i) SEQUENCE CHARACTERISTICS:
        (A) LENGTH: 30 bases
        (B) TYPE: nucleotide
        (C) STRANDEDNESS: single
        (D) TOPOLOGY: linear (ii) MOLECULE TYPE: synthetic DNA (vi) ORIGINAL SOURCE:
        (A) ORGANISM: human; serum infectious for PT-NANBH (vii) IMMEDIATE SOURCE:
        (A) LIBRARY: oligonucleotide synthesizer; oligo d137

(ix) FEATURE:
        (B) LOCATION: from 1 to 30 bases homologous to bases 154 to
            183 of the negative strand of BR11 (SEQ ID NO:5) bases
            174, 177 and 178 modified to introduce an EcoR1
            recognition site from 5 to 10 bases EcoR1 recognition
            site
        (D) OTHER INFORMATION: primes DNA synthesis on the positive
            strand of PT-NANBH genomic RNA/DNA and
            introduces an EcoR1 site for cloning.
```

(xi) SEQUENCE DESCRIPTION: SEQ ID NO:13:

GCGAGAATTC GGGATAGGTT GTCGCCTTCC                                              30

(2) INFORMATION FOR SEQ ID NO:14:

(i) SEQUENCE CHARACTERISTICS:
        (A) LENGTH: 27 bases
        (B) TYPE: nucleotide
        (C) STRANDEDNESS: single
        (D) TOPOLOGY: linear (ii) MOLECULE TYPE: synthetic DNA (vi) ORIGINAL SOURCE:
        (A) ORGANISM: human; serum infectious for PT-NANBH (vii) IMMEDIATE SOURCE:
        (A) LIBRARY: oligonucleotide synthesizer; oligo d136

(ix) FEATURE:
        (B) LOCATION: from 1 to 27 bases homologous to bases 672 to
            698 of the positive strand of BR11 (SEQ ID NO:5) base 675
            changed to G to introduce an EcoR1 recognition site
            from 4 to 9 bases EcoR1 recognition site
        (D) OTHER INFORMATION: primes DNA synthesis on the negative
            strand of PT-NANBH genomic RNA/DNA and introduces an
            EcoR1 site for cloning.

(xi) SEQUENCE DESCRIPTION: SEQ ID NO:14:

GGGGAATTCC TCCCGCTGCT GGGTAGC                                                 27

(2) INFORMATION FOR SEQ ID NO:15:

(i) SEQUENCE CHARACTERISTICS:
        (A) LENGTH: 28 bases
        (B) TYPE: nucleotide
        (C) STRANDEDNESS: single
        (D) TOPOLOGY: linear (ii) MOLECULE TYPE: synthetic DNA (vi) ORIGINAL SOURCE:
        (A) ORGANISM: chimpanzee; serum infectious for PT-NANBH (vii) IMMEDIATE SOURCE:
        (A) LIBRARY: oligonucleotide synthesizer; oligo d155

(ix) FEATURE:
        (B) LOCATION: from 1 to 28 bases homologous to bases 462 to
            489 of the negative strand of figure 47, European Patent
            Application 88310922.5; bases 483 and 485 changed to
            introduce an EcoR1 recognition site from 5 to 10 bases
            EcoR1 recognition site
        (D) OTHER INFORMATION: primes DNA synthesis on the positive
            strand of PT-NANBH genomic RNA/DNA and introduces an
            EcoR1 site for cloning.

(xi) SEQUENCE DESCRIPTION: SEQ ID NO:15:

ACGGGAATTC GACCAGGCAC CTGGGTGT                                                28

(2) INFORMATION FOR SEQ ID NO:16:

(i) SEQUENCE CHARACTERISTICS:
        (A) LENGTH: 23 bases
        (B) TYPE: nucleotide
        (C) STRANDEDNESS: single
        (D) TOPOLOGY: linear (ii) MOLECULE TYPE: synthetic DNA (vi) ORIGINAL SOURCE:
        (A) ORGANISM: chimpanzee; serum infectious for PT-NANBH

```
    (vii) IMMEDIATE SOURCE:
          (A) LIBRARY: oligonucleotide synthesizer; oligo d156

(ix) FEATURE:
          (B) LOCATION: from 1 to 23 bases homologous to bases 3315 to
              3337 of the positive strand of figure 47, European Patent
              Application 88310922.5; base 3323 changed to C to
              introduce an EcoR1 recognition site from 4 to 9 bases
              EcoR1 recognition site
          (D) OTHER INFORMATION: primes DNA synthesis on the negative
              strand of PT-NANBH genomic RNA/DNA and introduces an
              EcoR1 site for cloning.

(xi) SEQUENCE DESCRIPTION: SEQ ID NO:16:

CTTGAATTCT GGGAGGGCGT CTT                                               23

(2) INFORMATION FOR SEQ ID NO:17:

(i) SEQUENCE CHARACTERISTICS:
          (A) LENGTH: 29 bases
          (B) TYPE: nucleotide
          (C) STRANDEDNESS: single
          (D) TOPOLOGY: linear (ii) MOLECULE TYPE: synthetic DNA (vi) ORIGINAL SOURCE:
          (A) ORGANISM: human; serum infectious for PT-NANBH (vii) IMMEDIATE SOURCE:
          (A) LIBRARY: oligonucleotide synthesizer; oligo d92

(ix) FEATURE:
          (B) LOCATION: from 1 to 29 bases homologous to bases 36 to
              64 of the negative strand of JG2 (SEQ ID NO:3); bases 57,
              58 and 60 changed to introduce an EcoR1 recognition site
              from 5 to 10 bases EcoR1 recognition site
          (D) OTHER INFORMATION: primes DNA synthesis on the positive
              strand of PT-NANBH genomic RNA/DNA and introduces an
              EcoR1 site for cloning.

(xi) SEQUENCE DESCRIPTION: SEQ ID NO:17:

CGCCGAATTC ATGCCGCCAC AGGAGGTTG                                         29

(2) INFORMATION FOR SEQ ID NO:18:

(i) SEQUENCE CHARACTERISTICS:
          (A) LENGTH: 504 base pairs
          (B) TYPE: nucleotide with corresponding protein
          (C) STRANDEDNESS: single
          (D) TOPOLOGY: linear (ii) MOLECULE TYPE: cDNA to genomic RNA (vi) ORIGINAL SOURCE:
          (A) ORGANISM: human; serum infectious for PT-NANBH (vii) IMMEDIATE SOURCE:
          (A) LIBRARY: clone 164/137

(ix) FEATURE:
          (B) LOCATION: from 308 to 504 bp start of the PT-NANBH
              polyprotein
          (D) OTHER INFORMATION: probably encodes viral structural
              proteins (xi) SEQUENCE DESCRIPTION: SEQ ID NO:18:

GATCACTCCC CTGTGAGGAA CTACTGTCTT CACGCAGAAA GCGTCTAGCC ATGGCGTTAG       60

TATGAGTGTC GTGCAGCCTC CAGGACCCCC CCTCCCGGGA GAGCCATAGT GGTCTGCGGA      120

ACCGGTGAGT ACACCGGAAT TGCCAGGACG ACCGGGTCCT TCTTGGATT AACCCGCTCA       180
```

```
ATGCCTGGAG ATTTGGGCGT GCCCCCGCAA GACTGCTAGC CGAGTAGTGT TGGGTCGCGA      240

AAGGCCTTGT GGTACTGCCT GATAGGGTGC TTGCGAGTGC CCCGGGAGGT CTCGTAGACC      300

GTGCACC ATG AGC ACG AAT CCT AAA CCT CAA AGA AAA ACC AAA CGT AAC        349
        Met Ser Thr Asn Pro Lys Pro Gln Arg Lys Thr Lys Arg Asn
                         5                  10

ACC AAC CGC CGC CCA CAG GAC GTC AAG TTC CCG GGC GGT GGT CAG ATC        397
Thr Asn Arg Pro Gln Asp Val Lys Phe Pro Gly Gly Gly Gln Ile
 15              20                  25                  30

GTT GGT GGA GTT TAC CTG TTG CCG CGC AGG GGC CCC AGG TTG GGT GTG        445
Val Gly Gly Val Tyr Leu Leu Pro Arg Arg Gly Pro Arg Leu Gly Val
                 35                  40                  45

CGC GCG ACT AGG AAG ACT TCC GAG CGG TCG CAA CCT CGT GGA AGG CGA        493
Arg Ala Thr Arg Lys Thr Ser Glu Arg Ser Gln Pro Arg Gly Arg Arg
             50                  55                  60

CAA CCT ATC CC                                                          504
Gln Pro Ile Pro
         65
```

(2) INFORMATION FOR SEQ ID NO:19:

(i) SEQUENCE CHARACTERISTICS:
        (A) LENGTH: 1107 base pairs
        (B) TYPE: nucleotide with corresponding protein
        (C) STRANDEDNESS: single
        (D) TOPOLOGY: linear (ii) MOLECULE TYPE: cDNA to genomic RNA (vi) ORIGINAL SOURCE:
        (A) ORGANISM: human; serum infectious for PT-NANBH (vii) IMMEDIATE SOURCE:
        (A) LIBRARY: clone 136/155

(ix) FEATURE:
        (B) LOCATION: from 1 to 1107 bp portion of the PT-NANBH
            polyprotein
        (D) OTHER INFORMATION: probably encodes viral structural
            proteins (xi) SEQUENCE DESCRIPTION: SEQ ID NO:19:

```
TCC TCC CGC TGC TGG GTA GCG CTC ACT CCC ACG CTC GCG GCC AAG GAC         48
Ser Ser Arg Cys Trp Val Ala Leu Thr Pro Thr Leu Ala Ala Lys Asp
             5                  10                  15

GCC AGC ATC CCC ACT GCG ACA ATA CGA CGC CAC GTC GAT TTG CTC GTT         96
Ala Ser Ile Pro Thr Ala Thr Ile Arg Arg His Val Asp Leu Leu Val
                 20                  25                  30

GGG GCG GCT GCC TTC TGC TCC GCT ATG TAC GTG GGG GAT CTC TGC GGA        144
Gly Ala Ala Ala Phe Cys Ser Ala Met Tyr Val Gly Asp Leu Cys Gly
             35                  40                  45

TCT GTT TTC CTC GTC TCT CAG CTG TTC ACC TTC TCG CCT CGC CGA CAT        192
Ser Val Phe Leu Val Ser Gln Leu Phe Thr Phe Ser Pro Arg Arg His
         50                  55                  60

CAG ACG GTA CAG GAC TGC AAT TGT TCA ATC TAT CCC GGC CAC GTA TCA        240
Gln Thr Val Gln Asp Cys Asn Cys Ser Ile Tyr Pro Gly His Val Ser
 65                  70                  75                  80

GGT CAC CGC ATG GCT TGG GAT ATG ATG ATG AAC TGG TCA CCT ACA GCA        288
Gly His Arg Met Ala Trp Asp Met Met Met Asn Trp Ser Pro Thr Ala
                 85                  90                  95

GCC CTA GTG GTA TCG CAG CTA CTC CGG ATC CCA CAA GCT GTC GTG GAC        336
Ala Leu Val Val Ser Gln Leu Leu Arg Ile Pro Gln Ala Val Val Asp
                100                 105                 110

ATG GTG GCG GGG GCC CAC TGG GGA GTC CTG GCG GGC CTT GCC TAC TAT        384
Met Val Ala Gly Ala His Trp Gly Val Leu Ala Gly Leu Ala Tyr Tyr
```

-continued

|  |  | 115 |  |  | 120 |  |  | 125 |  |  |  |  |  |  |  |
|---|---|---|---|---|---|---|---|---|---|---|---|---|---|---|---|
| TCC | ATG | GTG | GGG | AAC | TGG | GCT | AAG | GTC | TTG | GTT | GTG | ATG | CTA | CTC | TTT | 432 |
| Ser | Met | Val | Gly | Asn | Trp | Ala | Lys | Val | Leu | Val | Val | Met | Leu | Leu | Phe |  |
|  | 130 |  |  |  | 135 |  |  |  | 140 |  |  |  |  |  |  |  |

```
TCC ATG GTG GGG AAC TGG GCT AAG GTC TTG GTT GTG ATG CTA CTC TTT    432
Ser Met Val Gly Asn Trp Ala Lys Val Leu Val Val Met Leu Leu Phe
    130             135             140

GCC GGC GTT GAC GGG GAA CCT TAC ACG ACA GGG GGG ACA CAC GGC CGC    480
Ala Gly Val Asp Gly Glu Pro Tyr Thr Thr Gly Gly Thr His Gly Arg
145             150             155             160

GCC GCC CAC GGG CTT ACA TCC CTC TTC ACA CCT GGG CCG GCT CAG AAA    528
Ala Ala His Gly Leu Thr Ser Leu Phe Thr Pro Gly Pro Ala Gln Lys
                165             170             175

ATC CAG CTT GTA AAC ACC AAC GGC AGC TGG CAC ATC AAC AGA ACT GCC    576
Ile Gln Leu Val Asn Thr Asn Gly Ser Trp His Ile Asn Arg Thr Ala
            180             185             190

TTG AAC TGC AAT GAC TCC CTC CAA ACT GGG TTC CTT GCC GCG CTG TTC    624
Leu Asn Cys Asn Asp Ser Leu Gln Thr Gly Phe Leu Ala Ala Leu Phe
        195             200             205

TAC ACG CAC AGG TTC AAT GCG TCC GGA TGC TCA GAG CGC ATG GCC AGC    672
Tyr Thr His Arg Phe Asn Ala Ser Gly Cys Ser Glu Arg Met Ala Ser
    210             215             220

TGC CGC CCC ATT GAC CAG TTC GAT CAG GGG TGG GGT CCC ATC ACT TAT    720
Cys Arg Pro Ile Asp Gln Phe Asp Gln Gly Trp Gly Pro Ile Thr Tyr
225             230             235             240

AAT GAG TCC CAC GGC TTG GAC CAG AGG CCC TAT TGC TGG CAC TAC GCA    768
Asn Glu Ser His Gly Leu Asp Gln Arg Pro Tyr Cys Trp His Tyr Ala
                245             250             255

CCT CAA CCG TGT GGT ATC GTG CCC GCG TTG CAG GTG TGT GGC CCA GTG    816
Pro Gln Pro Cys Gly Ile Val Pro Ala Leu Gln Val Cys Gly Pro Val
            260             265             270

TAC TGT TTC ACT CCA AGC CCT GTT GTG GTG GGG ACG ACC GAT CGT TTC    864
Tyr Cys Phe Thr Pro Ser Pro Val Val Val Gly Thr Thr Asp Arg Phe
        275             280             285

GGC GCC CCT ACG TAC AGA TGG GGT GAG AAT GAG ACG GAC GTG CTG CTT    912
Gly Ala Pro Thr Tyr Arg Trp Gly Glu Asn Glu Thr Asp Val Leu Leu
    290             295             300

CTC AAC AAC ACG CGG CCG CCA CGG GGC AAC TGG TTC GGC TGT ACA TGG    960
Leu Asn Asn Thr Arg Pro Pro Arg Gly Asn Trp Phe Gly Cys Thr Trp
305             310             315             320

ATG AAT AGC ACC GGG TTC ACC AAG ACG TGT GGG GGC CCC CCG TGC AAC    1008
Met Asn Ser Thr Gly Phe Thr Lys Thr Cys Gly Gly Pro Pro Cys Asn
                325             330             335

ATC GGG GGG GTC GGC AAC AAC ACT TTG ATC TGC CCC ACG GAC TGC TTC    1056
Ile Gly Gly Val Gly Asn Asn Thr Leu Ile Cys Pro Thr Asp Cys Phe
            340             345             350

CGG AAG CAT CCC GAG GCC ACT TAC ACC AAA TGC GGT TCG GGG CCT TGG    1104
Arg Lys His Pro Glu Ala Thr Tyr Thr Lys Cys Gly Ser Gly Pro Trp
        355             360             365

TTG                                                                1107
Leu
```

(2) INFORMATION FOR SEQ ID NO:20:

(i) SEQUENCE CHARACTERISTICS:
        (A) LENGTH: 2043 base pairs
        (B) TYPE: nucleotide with corresponding protein
        (C) STRANDEDNESS: single
        (D) TOPOLOGY: linear (ii) MOLECULE TYPE: cDNA to genomic RNA (vi) ORIGINAL SOURCE:
        (A) ORGANISM: human; serum infectious for PT-NANBH (vii) IMMEDIATE SOURCE:
   (A) LIBRARY: clone 156/92

(ix) FEATURE:
   (B) LOCATION: from 1 to 2043 bp portion of the PT-NANBH polyprotein
   (D) OTHER INFORMATION: probably encodes viral non-structural proteins (xi) SEQUENCE DESCRIPTION: SEQ ID NO:20:

```
TGG GAG GGC GTC TTC ACA GGC CTC ACC CAC GTG GAT GCC CAC TTC CTG        48
Trp Glu Gly Val Phe Thr Gly Leu Thr His Val Asp Ala His Phe Leu
              5                  10                  15

TCC CAA ACA AAG CAG GCA GGA GAC AAC TTC CCC TAC CTG GTG GCG TAC        96
Ser Gln Thr Lys Gln Ala Gly Asp Asn Phe Pro Tyr Leu Val Ala Tyr
                 20                  25                  30

CAG GCT ACT GTG TGC GCT AGG GCC CAG GCC CCA CCT CCA TCA TGG GAT       144
Gln Ala Thr Val Cys Ala Arg Ala Gln Ala Pro Pro Pro Ser Trp Asp
             35                  40                  45

CAA ATG TGG AAG TGT CTC ATA CGG CTA AAG CCT ACT CTG CGC GGG CCA       192
Gln Met Trp Lys Cys Leu Ile Arg Leu Lys Pro Thr Leu Arg Gly Pro
         50                  55                  60

ACA CCC TTG CTG TAT AGG CTG GGA GCC GTC CAA AAC GAG GTC ACC CTC       240
Thr Pro Leu Leu Tyr Arg Leu Gly Ala Val Gln Asn Glu Val Thr Leu
 65                  70                  75                  80

ACA CAC CCC ATA ACC AAA TTC ATC ATG GCA TGC ATG TCA GCC GAC CTG       288
Thr His Pro Ile Thr Lys Phe Ile Met Ala Cys Met Ser Ala Asp Leu
                 85                  90                  95

GAG GTC GTC ACG AGC ACC TGG GTG CTG GTG GGC GGG GTC CTT GCA GCT       336
Glu Val Val Thr Ser Thr Trp Val Leu Val Gly Gly Val Leu Ala Ala
            100                 105                 110

CTG GCT GCG TAT TGC TTG ACA ACA GGC AGC GTG GTC ATT GTG GGT AGG       384
Leu Ala Ala Tyr Cys Leu Thr Thr Gly Ser Val Val Ile Val Gly Arg
        115                 120                 125

ATC ATC TTG TCC GGG CGG CCG GCT ATT GTT CCC GAC AGG GAA GTC CTC       432
Ile Ile Leu Ser Gly Arg Pro Ala Ile Val Pro Asp Arg Glu Val Leu
130                 135                 140

TAC CAG GAG TTC GAT GAG ATG GAA GAG TGC GCG TCG CAC CTC CCT TAC       480
Tyr Gln Glu Phe Asp Glu Met Glu Glu Cys Ala Ser His Leu Pro Tyr
145                 150                 155                 160

ATC GAG CAG GGA ATG CAG CTC GCC GAG CAG TTC AAG CAA AAA GCG CTC       528
Ile Glu Gln Gly Met Gln Leu Ala Glu Gln Phe Lys Gln Lys Ala Leu
                165                 170                 175

GGG TTG CTG CAG ACA GCC ACC AAG CAA GCG GAG GCC GCT GCT CCC GTG       576
Gly Leu Leu Gln Thr Ala Thr Lys Gln Ala Glu Ala Ala Ala Pro Val
            180                 185                 190

GTG GAG TCC AAG TGG CGA GCC CTT GAG ACC TTC TGG GCG AAA CAC ATG       624
Val Glu Ser Lys Trp Arg Ala Leu Glu Thr Phe Trp Ala Lys His Met
        195                 200                 205

TGG AAC TTC ATC AGC GGG ATA CAG TAC TTA GCA GGC TTG TCC ACT CTG       672
Trp Asn Phe Ile Ser Gly Ile Gln Tyr Leu Ala Gly Leu Ser Thr Leu
    210                 215                 220

CCT GGG AAT CCC GCG ATT GCA TCA CTG ATG GCG TTC ACA GCC TCT GTC       720
Pro Gly Asn Pro Ala Ile Ala Ser Leu Met Ala Phe Thr Ala Ser Val
225                 230                 235                 240

ACT AGC CCG CTC ACC ACC CAA TCT ACC CTC CTG CTT AAC ATC CTG GGG       768
Thr Ser Pro Leu Thr Thr Gln Ser Thr Leu Leu Leu Asn Ile Leu Gly
                245                 250                 255

GGA TGG GTA GCC GCC CAA CTC GCT CCC CCC AGT GCT GCT TCA GCT TTC       816
Gly Trp Val Ala Ala Gln Leu Ala Pro Pro Ser Ala Ala Ser Ala Phe
            260                 265                 270
```

-continued

| | |
|---|---|
| GTA GGC GCC GGC ATT GCT GGT GCG GCT GTT GGC AGC ATA GGC CTT GGG<br>Val Gly Ala Gly Ile Ala Gly Ala Ala Val Gly Ser Ile Gly Leu Gly<br>275                             280                       285 | 864 |
| AAG GTG CTT GTG GAC ATC TTG GCG GGC TAT GGA GCA GGA GTG GCA GGC<br>Lys Val Leu Val Asp Ile Leu Ala Gly Tyr Gly Ala Gly Val Ala Gly<br>290                           295                       300 | 912 |
| GCG CTC GTG GCC TTT AAG GTC ATG AGC GGC GAA ATG CCC TCC ACC GAG<br>Ala Leu Val Ala Phe Lys Val Met Ser Gly Glu Met Pro Ser Thr Glu<br>305                           310                       315                320 | 960 |
| GAC CTG GTT AAC TTA CTC CCT GCC ATC CTC TCT CCT GGT GCC CTG GTC<br>Asp Leu Val Asn Leu Leu Pro Ala Ile Leu Ser Pro Gly Ala Leu Val<br>                    325                       330                       335 | 1008 |
| GTC GGG GTC GTG TGC GCA GCG ATA CTG CGT CGG CAC GTG GGT CCA GGG<br>Val Gly Val Val Cys Ala Ala Ile Leu Arg Arg His Val Gly Pro Gly<br>                      340                       345                     350 | 1056 |
| GAG GGG GCT GTG CAG TGG ATG AAC CGG CTG ATA GCG TTC GCC TCG CGG<br>Glu Gly Ala Val Gln Trp Met Asn Arg Leu Ile Ala Phe Ala Ser Arg<br>                    355                       360                     365 | 1104 |
| GGT AAC CAT GTT TCC CCC ACG CAC TAT GTG CCA GAG AGC GAC GCC GCA<br>Gly Asn His Val Ser Pro Thr His Tyr Val Pro Glu Ser Asp Ala Ala<br>370                           375                       380 | 1152 |
| GCA CGT GTC ACT CAG ATC CTC TCC GAC CTT ACT ATC ACC CAA CTG TTG<br>Ala Arg Val Thr Gln Ile Leu Ser Asp Leu Thr Ile Thr Gln Leu Leu<br>385                           390                       395                400 | 1200 |
| AAG AGG CTC CAC CAG TGG ATT AAC GAG GAC TGC TCC ACG CCC TGC TCC<br>Lys Arg Leu His Gln Trp Ile Asn Glu Asp Cys Ser Thr Pro Cys Ser<br>                    405                       410                     415 | 1248 |
| GGC TCG TGG CTA AGG GAT GTT TGG GAC TGG ATA TGC ACA GTT TTG GCT<br>Gly Ser Trp Leu Arg Asp Val Trp Asp Trp Ile Cys Thr Val Leu Ala<br>                    420                       425                     430 | 1296 |
| GAC TTC AAG ACC TGG CTC CAG TCC AAG CTC CTG CCG CGA TTA CCG GGA<br>Asp Phe Lys Thr Trp Leu Gln Ser Lys Leu Leu Pro Arg Leu Pro Gly<br>                    435                       440                     445 | 1344 |
| GTC CCC TTT TTC TCA TGC CAA CGT GGG TAC AAG GGG GTC TGG CGG GGA<br>Val Pro Phe Phe Ser Cys Gln Arg Gly Tyr Lys Gly Val Trp Arg Gly<br>450                           455                       460 | 1392 |
| GAC GGC ATC ATG CAG ACC ACC TGC TCA TGT GGA GCA CAG ATC ACC GGA<br>Asp Gly Ile Met Gln Thr Thr Cys Ser Cys Gly Ala Gln Ile Thr Gly<br>465                           470                       475                480 | 1440 |
| CAT GTC AAA AAC GGT TCC ATG AGG ATC GTT GGG CCT AAG ACC TGT AGT<br>His Val Lys Asn Gly Ser Met Arg Ile Val Gly Pro Lys Thr Cys Ser<br>                    485                       490                     495 | 1488 |
| AAC ATG TGG CAT GGA ACA TTC CCC ATC AAC GCA TAC ACC ACG GGC CCC<br>Asn Met Trp His Gly Thr Phe Pro Ile Asn Ala Tyr Thr Thr Gly Pro<br>                    500                       505                     510 | 1536 |
| TGC ACG CCC TCC CCA GCG CCA AAC TAT TCC AGG GCG CTG TGG CGG GTG<br>Cys Thr Pro Ser Pro Ala Pro Asn Tyr Ser Arg Ala Leu Trp Arg Val<br>                    515                       520                     525 | 1584 |
| GCT GCT GAG GAG TAC GTG GAG GTT ACG CGG GTG GGG GAT TTC CAC TAC<br>Ala Ala Glu Glu Tyr Val Glu Val Thr Arg Val Gly Asp Phe His Tyr<br>530                           535                       540 | 1632 |
| GTG ACG AGC ATG ACC ACT GAC AAC GTA AAA TGC CCG TGC CAG GTT CCA<br>Val Thr Ser Met Thr Thr Asp Asn Val Lys Cys Pro Cys Gln Val Pro<br>545                           550                       555                560 | 1680 |
| GCC CCC GAA TTC TTC ACA GAA GTG GAT GGG GTG CGG CTG CAC AGG TAC<br>Ala Pro Glu Phe Phe Thr Glu Val Asp Gly Val Arg Leu His Arg Tyr<br>                    565                       570                     575 | 1728 |
| GCT CCG GCG TGC AAA CCT CTC CTA CGG GAG GAG GTC ACA TTC CAG GTC<br>Ala Pro Ala Cys Lys Pro Leu Leu Arg Glu Glu Val Thr Phe Gln Val<br>                    580                       585                     590 | 1776 |

-continued

```
GGG CTC AAC CAA TAC CTG GTT GGG TCG CAG CTC CCA TGC GAG CCC GAA      1824
Gly Leu Asn Gln Tyr Leu Val Gly Ser Gln Leu Pro Cys Glu Pro Glu
            595                 600                 605

CCG GAT GTA GCA GTG CTC ACT TCC ATG CTC ACC GAC CCC TCC CAC ATC      1872
Pro Asp Val Ala Val Leu Thr Ser Met Leu Thr Asp Pro Ser His Ile
610                 615                 620

ACA GCA GAG ACG GCT AAG CGC AGG CTG GCC AGG GGG TCT CCC CCC TCC      1920
Thr Ala Glu Thr Ala Lys Arg Arg Leu Ala Arg Gly Ser Pro Pro Ser
625                 630                 635                 640

TTG GCC AGC TCT TCA GCT AGC CAG TTG TCT GCG CCT TCC TCG AAG GCG      1968
Leu Ala Ser Ser Ser Ala Ser Gln Leu Ser Ala Pro Ser Ser Lys Ala
            645                 650                 655

ACA TAC ATT ACC CAA AAT GAC TTC CCA GAC GCT GAC CTC ATC GAG GCC      2016
Thr Tyr Ile Thr Gln Asn Asp Phe Pro Asp Ala Asp Leu Ile Glu Ala
                660                 665                 670

AAC CTC CTG TGG CGG CAT GAG ATG GGC                                  2043
Asn Leu Leu Trp Arg His Glu Met Gly
            675                 680
```

(2) INFORMATION FOR SEQ ID NO:21:

(i) SEQUENCE CHARACTERISTICS:
        (A) LENGTH: 2116 base pairs
        (B) TYPE: nucleotide with corresponding protein
        (C) STRANDEDNESS: single
        (D) TOPOLOGY: linear (ii) MOLECULE TYPE: cDNA to genomic RNA (vi) ORIGINAL SOURCE:
        (A) ORGANISM: human; serum infectious for PT-NANBH (vii) IMMEDIATE SOURCE:
        (A) LIBRARY: cDNA clones from 5' end of the genome (ix) FEATURE:
        (B) LOCATION: from 308 to 2116 bp start of the PT-NANBH
            polyprotein
        (D) OTHER INFORMATION: viral structural and non-structural
            proteins (xi) SEQUENCE DESCRIPTION: SEQ ID NO:21:

```
GATCACTCCC CTGTGAGGAA CTACTGTCTT CACGCAGAAA GCGTCTAGCC ATGGCGTTAG      60

TATGAGTGTC GTGCAGCCTC CAGGACCCCC CCTCCCGGGA GAGCCATAGT GGTCTGCGGA     120

ACCGGTGAGT ACACCGGAAT TGCCAGGACG ACCGGGTCCT TCTTGGATT AACCCGCTCA      180

ATGCCTGGAG ATTTGGGCGT GCCCCCGCAA GACTGCTAGC CGAGTAGTGT TGGGTCGCGA     240

AAGGCCTTGT GGTACTGCCT GATAGGGTGC TTGCGAGTGC CCCGGGAGGT CTCGTAGACC     300

GTGCACC ATG AGC ACG AAT CCT AAA CCT CAA AGA AAA ACC AAA CGT AAC       349
        Met Ser Thr Asn Pro Lys Pro Gln Arg Lys Thr Lys Arg Asn
                        5                  10

ACC AAC CGC CGC CCA CAG GAC GTC AAG TTC CCG GGC GGT GGT CAG ATC       397
Thr Asn Pro Arg Pro Gln Asp Val Lys Phe Pro Gly Gly Gly Gln Ile
15                  20                  25                  30

GTT GGT GGA GTT TAC CTG TTG CCG CGC AGG GGC CCC AGG TTG GGT GTG       445
Val Gly Gly Val Tyr Leu Leu Pro Arg Arg Gly Pro Arg Leu Gly Val
                35                  40                  45

CGC GCG ACT AGG AAG ACT TCC GAG CGG TCG CAA CCT CGT GGA AGG CGA       493
Arg Ala Thr Arg Lys Thr Ser Glu Arg Ser Gln Pro Arg Gly Arg Arg
            50                  55                  60

CAA CCT ATC CCC AAG GCT CGC CAG CCC GAG GGC AGG GCC TGG GCT CAG       541
Gln Pro Ile Pro Lys Ala Arg Gln Pro Glu Gly Arg Ala Trp Ala Gln
            65                  70                  75
```

```
CCC GGG TAC CCT TGG CCC CTC TAT GGC AAC GAG GGC ATG GGG TGG GCA       589
Pro Gly Tyr Pro Trp Pro Leu Tyr Gly Asn Glu Gly Met Gly Trp Ala
 80                  85                  90

GGA TGG CTC CTG TCA CCC CGT GGC TCC CGG CCT AGT TGG GGC CCC ACT       637
Gly Trp Leu Leu Ser Pro Arg Gly Ser Arg Pro Ser Trp Gly Pro Thr
100                 105                 110                 115

GAC CCC CGG CGT AGG TCG CGT AAT TTG GGT AAA GTC ATC GAT ACC CTC       685
Asp Pro Arg Arg Arg Ser Arg Asn Leu Gly Lys Val Ile Asp Thr Leu
                120                 125                 130

ACA TGC GGC TTC GCC GAC CTC ATG GGG TAC ATT CCG CTC GTC GGC GCT       733
Thr Cys Gly Phe Ala Asp Leu Met Gly Tyr Ile Pro Leu Val Gly Ala
            135                 140                 145

CCC TTA GGG GGC GCT GCC AGG GCC CTG GCG CAT GGC GTC CGG GTT CTG       781
Pro Leu Gly Gly Ala Ala Arg Ala Leu Ala His Gly Val Arg Val Leu
        150                 155                 160

GAG GAC GGC GTG AAC TAT GCA ACA GGG AAT TTA CCC GGT TGC TCT TTC       829
Glu Asp Gly Val Asn Tyr Ala Thr Gly Asn Leu Pro Gly Cys Ser Phe
    165                 170                 175

TCT ATC TTC CTC TTG GCT TTG CTG TCC TGT TTG ACC ATT CCA GCT TCC       877
Ser Ile Phe Leu Leu Ala Leu Leu Ser Cys Leu Thr Ile Pro Ala Ser
180                 185                 190                 195

GCT TAT GAA GTG CGC AAC GTG TCC GGG ATC TAC CAT GTC ACG AAC GAT       925
Ala Tyr Glu Val Arg Asn Val Ser Gly Ile Tyr His Val Thr Asn Asp
                200                 205                 210

TGC TCC AAC TCA AGC ATC GTG TAC GAG ACA GCG GAC ATG ATC ATG CAC       973
Cys Ser Asn Ser Ser Ile Val Tyr Glu Thr Ala Asp Met Ile Met His
            215                 220                 225

ACC CCC GGG TGT GTG CCC TGT GTC CGG GAG GGT AAT TCC TCC CGC TGC      1021
Thr Pro Gly Cys Val Pro Cys Val Arg Glu Gly Asn Ser Ser Arg Cys
        230                 235                 240

TGG GTA GCG CTC ACT CCC ACG CTC GCG GCC AAG GAC GCC AGC ATC CCC      1069
Trp Val Ala Leu Thr Pro Thr Leu Ala Ala Lys Asp Ala Ser Ile Pro
    245                 250                 255

ACT GCG ACA ATA CGA CGC CAC GTC GAT TTG CTC GTT GGG GCG GCT GCC      1117
Thr Ala Thr Ile Arg Arg His Val Asp Leu Leu Val Gly Ala Ala Ala
260                 265                 270                 275

TTC TGC TCC GCT ATG TAC GTG GGG GAT CTC TGC GGA TCT GTT TTC CTC      1165
Phe Cys Ser Ala Met Tyr Val Gly Asp Leu Cys Gly Ser Val Phe Leu
                280                 285                 290

GTC TCT CAG CTG TTC ACC TTC TCG CCT CGC CGA CAT CAG ACG GTA CAG      1213
Val Ser Gln Leu Phe Thr Phe Ser Pro Arg Arg His Gln Thr Val Gln
            295                 300                 305

GAC TGC AAT TGT TCA ATC TAT CCC GGC CAC GTA TCA GGT CAC CGC ATG      1261
Asp Cys Asn Cys Ser Ile Tyr Pro Gly His Val Ser Gly His Arg Met
        310                 315                 320

GCT TGG GAT ATG ATG ATG AAC TGG TCA CCT ACA GCA GCC CTA GTG GTA      1309
Ala Trp Asp Met Met Met Asn Trp Ser Pro Thr Ala Ala Leu Val Val
    325                 330                 335

TCG CAG CTA CTC CGG ATC CCA CAA GCT GTC GTG GAC ATG GTG GCG GGG      1357
Ser Gln Leu Leu Arg Ile Pro Gln Ala Val Val Asp Met Val Ala Gly
340                 345                 350                 355

GCC CAC TGG GGA GTC CTG GCG GGC CTT GCC TAC TAT TCC ATG GTG GGG      1405
Ala His Trp Gly Val Leu Ala Gly Leu Ala Tyr Tyr Ser Met Val Gly
                360                 365                 370

AAC TGG GCT AAG GTC TTG GTT GTG ATG CTA CTC TTT GCC GGC GTT GAC      1453
Asn Trp Ala Lys Val Leu Val Val Met Leu Leu Phe Ala Gly Val Asp
            375                 380                 385

GGG GAA CCT TAC ACG ACA GGG GGG ACA CAC GGC CGC GCC GCC CAC GGG      1501
Gly Glu Pro Tyr Thr Thr Gly Gly Thr His Gly Arg Ala Ala His Gly
```

```
                390             395             400
CTT ACA TCC CTC TTC ACA CCT GGG CCG GCT CAG AAA ATC CAG CTT GTA         1549
Leu Thr Ser Leu Phe Thr Pro Gly Pro Ala Gln Lys Ile Gln Leu Val
    405                 410                 415

AAC ACC AAC GGC AGC TGG CAC ATC AAC AGA ACT GCC TTG AAC TGC AAT         1597
Asn Thr Asn Gly Ser Trp His Ile Asn Arg Thr Ala Leu Asn Cys Asn
420                 425                 430                 435

GAC TCC CTC CAA ACT GGG TTC CTT GCC GCG CTG TTC TAC ACG CAC AGG         1645
Asp Ser Leu Gln Thr Gly Phe Leu Ala Ala Leu Phe Tyr Thr His Arg
                440                 445                 450

TTC AAT GCG TCC GGA TGC TCA GAG CGC ATG GCC AGC TGC CGC CCC ATT         1693
Phe Asn Ala Ser Gly Cys Ser Glu Arg Met Ala Ser Cys Arg Pro Ile
            455                 460                 465

GAC CAG TTC GAT CAG GGG TGG GGT CCC ATC ACT TAT AAT GAG TCC CAC         1741
Asp Gln Phe Asp Gln Gly Trp Gly Pro Ile Thr Tyr Asn Glu Ser His
        470                 475                 480

GGC TTG GAC CAG AGG CCC TAT TGC TGG CAC TAC GCA CCT CAA CCG TGT         1789
Gly Leu Asp Gln Arg Pro Tyr Cys Trp His Tyr Ala Pro Gln Pro Cys
    485                 490                 495

GGT ATC GTG CCC GCG TTG CAG GTG TGT GGC CCA GTG TAC TGT TTC ACT         1837
Gly Ile Val Pro Ala Leu Gln Val Cys Gly Pro Val Tyr Cys Phe Thr
500                 505                 510                 515

CCA AGC CCT GTT GTG GTG GGG ACG ACC GAT CGT TTC GGC GCC CCT ACG         1885
Pro Ser Pro Val Val Val Gly Thr Thr Asp Arg Phe Gly Ala Pro Thr
                520                 525                 530

TAC AGA TGG GGT GAG AAT GAG ACG GAC GTG CTG CTT CTC AAC AAC ACG         1933
Tyr Arg Trp Gly Glu Asn Glu Thr Asp Val Leu Leu Leu Asn Asn Thr
                535                 540                 545

CGG CCG CCA CGG GGC AAC TGG TTC GGC TGT ACA TGG ATG AAT AGC ACC         1981
Arg Pro Pro Arg Gly Asn Trp Phe Gly Cys Thr Trp Met Asn Ser Thr
            550                 555                 560

GGG TTC ACC AAG ACG TGT GGG GGC CCC CCG TGC AAC ATC GGG GGG GTC         2029
Gly Phe Thr Lys Thr Cys Gly Gly Pro Pro Cys Asn Ile Gly Gly Val
        565                 570                 575

GGC AAC AAC ACT TTG ATC TGC CCC ACG GAC TGC TTC CGG AAG CAT CCC         2077
Gly Asn Asn Thr Leu Ile Cys Pro Thr Asp Cys Phe Arg Lys His Pro
580                 585                 590                 595

GAG GCC ACT TAC ACC AAA TGC GGT TCG GGG CCT TGG TTG                     2116
Glu Ala Thr Tyr Thr Lys Cys Gly Ser Gly Pro Trp Leu
                600                 605
```

(2) INFORMATION FOR SEQ ID NO:22:

(i) SEQUENCE CHARACTERISTICS:
        (A) LENGTH: 3750 base pairs
        (B) TYPE: nucleotide with corresponding protein
        (C) STRANDEDNESS: single
        (D) TOPOLOGY: linear (ii) MOLECULE TYPE: cDNA to genomic RNA (vi) ORIGINAL SOURCE:
        (A) ORGANISM: human; serum infectious for PT-NANBH (vii) IMMEDIATE SOURCE:
        (A) LIBRARY: cDNA clones from 3' end of the genome (ix) FEATURE:
        (B) LOCATION: from 1 to 3750 bp portion of the PT-NANBH
            polyprotein
        (D) OTHER INFORMATION: viral non-structural proteins (xi) SEQUENCE DESCRIPTION: SEQ ID NO:22:

```
TGG GAG GGC GTC TTC ACA GGC CTC ACC CAC GTG GAT GCC CAC TTC CTG         48
```

-continued

| | | | | | | | | | | | | | | | | |
|---|---|---|---|---|---|---|---|---|---|---|---|---|---|---|---|---|
| | Trp | Glu | Gly | Val | Phe | Thr | Gly | Leu | Thr | His | Val | Asp | Ala | His | Phe | Leu |
| | | | | 5 | | | | | 10 | | | | | 15 | | |

| | | | | | | | | | | | | | | | | |
|---|---|---|---|---|---|---|---|---|---|---|---|---|---|---|---|---|
| TCC | CAA | ACA | AAG | CAG | GCA | GGA | GAC | AAC | TTC | CCC | TAC | CTG | GTG | GCG | TAC | 96 |
| Ser | Gln | Thr | Lys | Gln | Ala | Gly | Asp | Asn | Phe | Pro | Tyr | Leu | Val | Ala | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| CAG | GCT | ACT | GTG | TGC | GCT | AGG | GCC | CAG | GCC | CCA | CCT | CCA | TCA | TGG | GAT | 144 |
| Gln | Ala | Thr | Val | Cys | Ala | Arg | Ala | Gln | Ala | Pro | Pro | Pro | Ser | Trp | Asp | |
| | | 35 | | | | | 40 | | | | | 45 | | | | |

| | | | | | | | | | | | | | | | | |
|---|---|---|---|---|---|---|---|---|---|---|---|---|---|---|---|---|
| CAA | ATG | TGG | AAG | TGT | CTC | ATA | CGG | CTA | AAG | CCT | ACT | CTG | CGC | GGG | CCA | 192 |
| Gln | Met | Trp | Lys | Cys | Leu | Ile | Arg | Leu | Lys | Pro | Thr | Leu | Arg | Gly | Pro | |
| | 50 | | | | | 55 | | | | | 60 | | | | | |

| | | | | | | | | | | | | | | | | |
|---|---|---|---|---|---|---|---|---|---|---|---|---|---|---|---|---|
| ACA | CCC | TTG | CTG | TAT | AGG | CTG | GGA | GCC | GTC | CAA | AAC | GAG | GTC | ACC | CTC | 240 |
| Thr | Pro | Leu | Leu | Tyr | Arg | Leu | Gly | Ala | Val | Gln | Asn | Glu | Val | Thr | Leu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ACA | CAC | CCC | ATA | ACC | AAA | TTC | ATC | ATG | GCA | TGC | ATG | TCA | GCC | GAC | CTG | 288 |
| Thr | His | Pro | Ile | Thr | Lys | Phe | Ile | Met | Ala | Cys | Met | Ser | Ala | Asp | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| GAG | GTC | GTC | ACG | AGC | ACC | TGG | GTG | CTG | GTG | GGC | GGG | GTC | CTT | GCA | GCT | 336 |
| Glu | Val | Val | Thr | Ser | Thr | Trp | Val | Leu | Val | Gly | Gly | Val | Leu | Ala | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| CTG | GCT | GCG | TAT | TGC | TTG | ACA | ACA | GGC | AGC | GTG | GTC | ATT | GTG | GGT | AGG | 384 |
| Leu | Ala | Ala | Tyr | Cys | Leu | Thr | Thr | Gly | Ser | Val | Val | Ile | Val | Gly | Arg | |
| | | 115 | | | | | 120 | | | | | 125 | | | | |

| | | | | | | | | | | | | | | | | |
|---|---|---|---|---|---|---|---|---|---|---|---|---|---|---|---|---|
| ATC | ATC | TTG | TCC | GGG | CGG | CCG | GCT | ATT | GTT | CCC | GAC | AGG | GAA | GTC | CTC | 432 |
| Ile | Ile | Leu | Ser | Gly | Arg | Pro | Ala | Ile | Val | Pro | Asp | Arg | Glu | Val | Leu | |
| | 130 | | | | | 135 | | | | | 140 | | | | | |

| | | | | | | | | | | | | | | | | |
|---|---|---|---|---|---|---|---|---|---|---|---|---|---|---|---|---|
| TAC | CAG | GAG | TTC | GAT | GAG | ATG | GAA | GAG | TGC | GCG | TCG | CAC | CTC | CCT | TAC | 480 |
| Tyr | Gln | Glu | Phe | Asp | Glu | Met | Glu | Glu | Cys | Ala | Ser | His | Leu | Pro | Tyr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ATC | GAG | CAG | GGA | ATG | CAG | CTC | GCC | GAG | CAG | TTC | AAG | CAA | AAA | GCG | CTC | 528 |
| Ile | Glu | Gln | Gly | Met | Gln | Leu | Ala | Glu | Gln | Phe | Lys | Gln | Lys | Ala | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| GGG | TTG | CTG | CAG | ACA | GCC | ACC | AAG | CAA | GCG | GAG | GCC | GCT | GCT | CCC | GTG | 576 |
| Gly | Leu | Leu | Gln | Thr | Ala | Thr | Lys | Gln | Ala | Glu | Ala | Ala | Ala | Pro | Val | |
| | | | | 180 | | | | | 185 | | | | | 190 | | |

| | | | | | | | | | | | | | | | | |
|---|---|---|---|---|---|---|---|---|---|---|---|---|---|---|---|---|
| GTG | GAG | TCC | AAG | TGG | CGA | GCC | CTT | GAG | ACC | TTC | TGG | GCG | AAA | CAC | ATG | 624 |
| Val | Glu | Ser | Lys | Trp | Arg | Ala | Leu | Glu | Thr | Phe | Trp | Ala | Lys | His | Met | |
| | | | 195 | | | | | 200 | | | | | 205 | | | |

| | | | | | | | | | | | | | | | | |
|---|---|---|---|---|---|---|---|---|---|---|---|---|---|---|---|---|
| TGG | AAC | TTC | ATC | AGC | GGG | ATA | CAG | TAC | TTA | GCA | GGC | TTG | TCC | ACT | CTG | 672 |
| Trp | Asn | Phe | Ile | Ser | Gly | Ile | Gln | Tyr | Leu | Ala | Gly | Leu | Ser | Thr | Leu | |
| | | | 210 | | | | | 215 | | | | | 220 | | | |

| | | | | | | | | | | | | | | | | |
|---|---|---|---|---|---|---|---|---|---|---|---|---|---|---|---|---|
| CCT | GGG | AAT | CCC | GCG | ATT | GCA | TCA | CTG | ATG | GCG | TTC | ACA | GCC | TCT | GTC | 720 |
| Pro | Gly | Asn | Pro | Ala | Ile | Ala | Ser | Leu | Met | Ala | Phe | Thr | Ala | Ser | Val | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ACT | AGC | CCG | CTC | ACC | ACC | CAA | TCT | ACC | CTC | CTG | CTT | AAC | ATC | CTG | GGG | 768 |
| Thr | Ser | Pro | Leu | Thr | Thr | Gln | Ser | Thr | Leu | Leu | Leu | Asn | Ile | Leu | Gly | |
| | | | | 245 | | | | | 250 | | | | | 255 | | |

| | | | | | | | | | | | | | | | | |
|---|---|---|---|---|---|---|---|---|---|---|---|---|---|---|---|---|
| GGA | TGG | GTA | GCC | GCC | CAA | CTC | GCT | CCC | CCC | AGT | GCT | GCT | TCA | GCT | TTC | 816 |
| Gly | Trp | Val | Ala | Ala | Gln | Leu | Ala | Pro | Pro | Ser | Ala | Ala | Ser | Ala | Phe | |
| | | | 260 | | | | | 265 | | | | | 270 | | | |

| | | | | | | | | | | | | | | | | |
|---|---|---|---|---|---|---|---|---|---|---|---|---|---|---|---|---|
| GTA | GGC | GCC | GGC | ATT | GCT | GGT | GCG | GCT | GTT | GGC | AGC | ATA | GGC | CTT | GGG | 864 |
| Val | Gly | Ala | Gly | Ile | Ala | Gly | Ala | Ala | Val | Gly | Ser | Ile | Gly | Leu | Gly | |
| | | | 275 | | | | | 280 | | | | | 285 | | | |

| | | | | | | | | | | | | | | | | |
|---|---|---|---|---|---|---|---|---|---|---|---|---|---|---|---|---|
| AAG | GTG | CTT | GTG | GAC | ATC | TTG | GCG | GGC | TAT | GGA | GCA | GGA | GTG | GCA | GGC | 912 |
| Lys | Val | Leu | Val | Asp | Ile | Leu | Ala | Gly | Tyr | Gly | Ala | Gly | Val | Ala | Gly | |
| | | | 290 | | | | | 295 | | | | | 300 | | | |

| | | | | | | | | | | | | | | | | |
|---|---|---|---|---|---|---|---|---|---|---|---|---|---|---|---|---|
| GCG | CTC | GTG | GCC | TTT | AAG | GTC | ATG | AGC | GGC | GAA | ATG | CCC | TCC | ACC | GAG | 960 |
| Ala | Leu | Val | Ala | Phe | Lys | Val | Met | Ser | Gly | Glu | Met | Pro | Ser | Thr | Glu | |
| 305 | | | | | 310 | | | | | 315 | | | | | 320 | |

```
                                                        -continued

GAC CTG GTT AAC TTA CTC CCT GCC ATC CTC TCT CCT GGT GCC CTG GTC              1008
Asp Leu Val Asn Leu Leu Pro Ala Ile Leu Ser Pro Gly Ala Leu Val
            325                 330                 335

GTC GGG GTC GTG TGC GCA GCG ATA CTG CGT CGG CAC GTG GGT CCA GGG              1056
Val Gly Val Val Cys Ala Ala Ile Leu Arg Arg His Val Gly Pro Gly
            340                 345                 350

GAG GGG GCT GTG CAG TGG ATG AAC CGG CTG ATA GCG TTC GCC TCG CGG              1104
Glu Gly Ala Val Gln Trp Met Asn Arg Leu Ile Ala Phe Ala Ser Arg
            355                 360                 365

GGT AAC CAT GTT TCC CCC ACG CAC TAT GTG CCA GAG AGC GAC GCC GCA              1152
Gly Asn His Val Ser Pro Thr His Tyr Val Pro Glu Ser Asp Ala Ala
            370                 375                 380

GCA CGT GTC ACT CAG ATC CTC TCC GAC CTT ACT ATC ACC CAA CTG TTG              1200
Ala Arg Val Thr Gln Ile Leu Ser Asp Leu Thr Ile Thr Gln Leu Leu
385                 390                 395                 400

AAG AGG CTC CAC CAG TGG ATT AAC GAG GAC TGC TCC ACG CCC TGC TCC              1248
Lys Arg Leu His Gln Trp Ile Asn Glu Asp Cys Ser Thr Pro Cys Ser
            405                 410                 415

GGC TCG TGG CTA AGG GAT GTT TGG GAC TGG ATA TGC ACA GTT TTG GCT              1296
Gly Ser Trp Leu Arg Asp Val Trp Asp Trp Ile Cys Thr Val Leu Ala
            420                 425                 430

GAC TTC AAG ACC TGG CTC CAG TCC AAG CTC CTG CCG CGA TTA CCG GGA              1344
Asp Phe Lys Thr Trp Leu Gln Ser Lys Leu Leu Pro Arg Leu Pro Gly
            435                 440                 445

GTC CCC TTT TTC TCA TGC CAA CGT GGG TAC AAG GGG GTC TGG CGG GGA              1392
Val Pro Phe Phe Ser Cys Gln Arg Gly Tyr Lys Gly Val Trp Arg Gly
            450                 455                 460

GAC GGC ATC ATG CAG ACC ACC TGC TCA TGT GGA GCA CAG ATC ACC GGA              1440
Asp Gly Ile Met Gln Thr Thr Cys Ser Cys Gly Ala Gln Ile Thr Gly
465                 470                 475                 480

CAT GTC AAA AAC GGT TCC ATG AGG ATC GTT GGG CCT AAG ACC TGT AGT              1488
His Val Lys Asn Gly Ser Met Arg Ile Val Gly Pro Lys Thr Cys Ser
            485                 490                 495

AAC ATG TGG CAT GGA ACA TTC CCC ATC AAC GCA TAC ACC ACG GGC CCC              1536
Asn Met Trp His Gly Thr Phe Pro Ile Asn Ala Tyr Thr Thr Gly Pro
            500                 505                 510

TGC ACG CCC TCC CCA GCG CCA AAC TAT TCC AGG GCG CTG TGG CGG GTG              1584
Cys Thr Pro Ser Pro Ala Pro Asn Tyr Ser Arg Ala Leu Trp Arg Val
            515                 520                 525

GCT GCT GAG GAG TAC GTG GAG GTT ACG CGG GTG GGG GAT TTC CAC TAC              1632
Ala Ala Glu Glu Tyr Val Glu Val Thr Arg Val Gly Asp Phe His Tyr
            530                 535                 540

GTG ACG AGC ATG ACC ACT GAC AAC GTA AAA TGC CCG TGC CAG GTT CCA              1680
Val Thr Ser Met Thr Thr Asp Asn Val Lys Cys Pro Cys Gln Val Pro
545                 550                 555                 560

GCC CCC GAA TTC TTC ACA GAA GTG GAT GGG GTG CGG CTG CAC AGG TAC              1728
Ala Pro Glu Phe Phe Thr Glu Val Asp Gly Val Arg Leu His Arg Tyr
            565                 570                 575

GCT CCG GCG TGC AAA CCT CTC CTA CGG GAG GAG GTC ACA TTC CAG GTC              1776
Ala Pro Ala Cys Lys Pro Leu Leu Arg Glu Glu Val Thr Phe Gln Val
            580                 585                 590

GGG CTC AAC CAA TAC CTG GTT GGG TCG CAG CTC CCA TGC GAG CCC GAA              1824
Gly Leu Asn Gln Tyr Leu Val Gly Ser Gln Leu Pro Cys Glu Pro Glu
            595                 600                 605

CCG GAT GTA GCA GTG CTC ACT TCC ATG CTC ACC GAC CCC TCC CAC ATC              1872
Pro Asp Val Ala Val Leu Thr Ser Met Leu Thr Asp Pro Ser His Ile
            610                 615                 620

ACA GCA GAG ACG GCT AAG CGC AGG CTG GCC AGG GGG TCT CCC CCC TCC             1920
Thr Ala Glu Thr Ala Lys Arg Arg Leu Ala Arg Gly Ser Pro Pro Ser
625                 630                 635                 640
```

-continued

| | | |
|---|---|---|
| TTG GCC AGC TCT TCA GCT AGC CAG TTG TCT GCG CCT TCC TCG AAG GCG<br>Leu Ala Ser Ser Ser Ala Ser Gln Leu Ser Ala Pro Ser Ser Lys Ala<br>                          645                      650                    655 | | 1968 |
| ACA TAC ATT ACC CAA AAT GAC TTC CCA GAC GCT GAC CTC ATC GAG GCC<br>Thr Tyr Ile Thr Gln Asn Asp Phe Pro Asp Ala Asp Leu Ile Glu Ala<br>                   660                      665                   670 | | 2016 |
| AAC CTC CTG TGG CGG CAT GAG ATG GGC GGG GAC ATT ACC CGC GTG GAG<br>Asn Leu Leu Trp Arg His Glu Met Gly Gly Asp Ile Thr Arg Val Glu<br>                675                      680                  685 | | 2064 |
| TCA GAG AAC AAG GTA GTA ATC CTG GAC TCT TTC GAC CCG CTC CGA GCG<br>Ser Glu Asn Lys Val Val Ile Leu Asp Ser Phe Asp Pro Leu Arg Ala<br>690                      695                      700 | | 2112 |
| GAG GAG GAT GAG CGG GAA GTG TCC GTC CCG GCG GAG ATC CTG CGG AAA<br>Glu Glu Asp Glu Arg Glu Val Ser Val Pro Ala Glu Ile Leu Arg Lys<br>705                      710                      715                  720 | | 2160 |
| TCC AAG AAA TTC CCA CCA GCG ATG CCC GCA TGG GCA CGC CCG GAT TAC<br>Ser Lys Lys Phe Pro Pro Ala Met Pro Ala Trp Ala Arg Pro Asp Tyr<br>                   725                      730                   735 | | 2208 |
| AAC CCT CCG CTG CTG GAG TCC TGG AAG GCC CCG GAC TAC GTC CCT CCA<br>Asn Pro Pro Leu Leu Glu Ser Trp Lys Ala Pro Asp Tyr Val Pro Pro<br>                740                      745                  750 | | 2256 |
| GTG GTA CAT GGG TGC CCA CTG CCA CCT ACT AAG ACC CCT CCT ATA CCA<br>Val Val His Gly Cys Pro Leu Pro Pro Thr Lys Thr Pro Pro Ile Pro<br>                   755                      760                  765 | | 2304 |
| CCT CCA CGG AGG AAG AGG ACA GTT GTT CTG ACA GAA TCC ACC GTG TCT<br>Pro Pro Arg Arg Lys Arg Thr Val Val Leu Thr Glu Ser Thr Val Ser<br>        770                      775                      780 | | 2352 |
| TCT GCC CTG GCG GAG CTT GCC ACA AAG GCT TTC GGT AGC TCC GAA CCG<br>Ser Ala Leu Ala Glu Leu Ala Thr Lys Ala Phe Gly Ser Ser Glu Pro<br>785                      790                      795                  800 | | 2400 |
| TCG GCC GTC GAC AGC GGC ACG GCA ACC GCC CCT CCT GAC CAA CCC TCC<br>Ser Ala Val Asp Ser Gly Thr Ala Thr Ala Pro Pro Asp Gln Pro Ser<br>                   805                      810                  815 | | 2448 |
| GAC GAC GGC GGA GCA GGA TCT GAC GTT GAG TCG TAT TCC TCC ATG CCC<br>Asp Asp Gly Gly Ala Gly Ser Asp Val Glu Ser Tyr Ser Ser Met Pro<br>                   820                      825                  830 | | 2496 |
| CCC CTT GAG GGG GAG CCG GGG GAC CCC GAT CTC AGC GAC GGG TCT TGG<br>Pro Leu Glu Gly Glu Pro Gly Asp Pro Asp Leu Ser Asp Gly Ser Trp<br>                835                      840                  845 | | 2544 |
| TCT ACC GTG AGT GAG GAG GCC GGT GAG GAC GTC GTC TGC TGC TCG ATG<br>Ser Thr Val Ser Glu Glu Ala Gly Glu Asp Val Val Cys Cys Ser Met<br>850                      855                      860 | | 2592 |
| TCC TAC ACA TGG ACA GGC GCT CTG ATC ACG CCA TGC GCT GCG GAG GAA<br>Ser Tyr Thr Trp Thr Gly Ala Leu Ile Thr Pro Cys Ala Ala Glu Glu<br>865                      870                      875                  880 | | 2640 |
| AGC AAG CTG CCC ATC AAC GCG TTG AGC AAC TCT TTG CTG CGT CAC CAC<br>Ser Lys Leu Pro Ile Asn Ala Leu Ser Asn Ser Leu Leu Arg His His<br>                   885                      890                  895 | | 2688 |
| AAC ATG GTC TAC GCT ACC ACA TCC CGC AGC GCA AGC CAG CGG CAG AAG<br>Asn Met Val Tyr Ala Thr Thr Ser Arg Ser Ala Ser Gln Arg Gln Lys<br>                   900                      905                  910 | | 2736 |
| AAG GTC ACC TTT GAC AGA CTG CAA ATC CTG GAC GAT CAC TAC CAG GAC<br>Lys Val Thr Phe Asp Arg Leu Gln Ile Leu Asp Asp His Tyr Gln Asp<br>                915                      920                  925 | | 2784 |
| GTG CTC AAG GAG ATG AAG GCG AAG GCG TCC ACA GTT AAG GCT AAG CTT<br>Val Leu Lys Glu Met Lys Ala Lys Ala Ser Thr Val Lys Ala Lys Leu<br>930                      935                      940 | | 2832 |
| CTA TCA GTA GAG GAA GCC TGC AAG CTG ACG CCC CCA CAT TCG GCC AAA<br>Leu Ser Val Glu Glu Ala Cys Lys Leu Thr Pro Pro His Ser Ala Lys | | 2880 |

-continued

```
                945                950                955                960
TCT AAA TTT GGC TAT GGG GCA AAG GAC GTC CGG AAC CTA TCC AGC AAG                2928
Ser Lys Phe Gly Tyr Gly Ala Lys Asp Val Arg Asn Leu Ser Ser Lys
                    965                970                975

GCC ATT AAC CAC ATC CGC TCC GTG TGG GAG GAC TTG TTG GAA GAC ACT                2976
Ala Ile Asn His Ile Arg Ser Val Trp Glu Asp Leu Leu Glu Asp Thr
            980                985                990

GAA ACA CCA ATT GAC ACC ACC ATC ATG GCA AAA AAT GAG GTT TTC TGC                3024
Glu Thr Pro Ile Asp Thr Thr Ile Met Ala Lys Asn Glu Val Phe Cys
            995                1000                1005

GTC CAA CCA GAG AGA GGA GGC CGC AAG CCA GCT CGC CTT ATC GTG TTC                3072
Val Gln Pro Glu Arg Gly Gly Arg Lys Pro Ala Arg Leu Ile Val Phe
        1010                1015                1020

CCA GAC TTG GGG TCC CGT GTG TGC GAG AAA ATG GCC CTC TAT GAC GTG                3120
Pro Asp Leu Gly Val Arg Val Cys Glu Lys Met Ala Leu Tyr Asp Val
1025                1030                1035                1040

GTC TCC ACC CTC CCT CAG GCT GTG ATG GGC TCC TCG TAC GGA TTC CAG                3168
Val Ser Thr Leu Pro Gln Ala Val Met Gly Ser Ser Tyr Gly Phe Gln
                    1045                1050                1055

TAT TCT CCT GGA CAG CGG GTC GAG TTC CTG GTG AAC GCC TGG AAA TCA                3216
Tyr Ser Pro Gly Gln Arg Val Glu Phe Leu Val Asn Ala Trp Lys Ser
                1060                1065                1070

AAG AAG ACC CCT ATG GGC TTT GCA TAT GAC ACC CGC TGT TTT GAC TCA                3264
Lys Lys Thr Pro Met Gly Phe Ala Tyr Asp Thr Arg Cys Phe Asp Ser
            1075                1080                1085

ACA GTC ACT GAG AAT GAC ATC CGT GTA GAG GAG TCA ATT TAT CAA TGT                3312
Thr Val Thr Glu Asn Asp Ile Arg Val Glu Glu Ser Ile Tyr Gln Cys
        1090                1095                1100

TGT GAC TTG GCC CCC GAA GCC AGA CAG GCC ATA AGG TCG CTC ACA GAG                3360
Cys Asp Leu Ala Pro Glu Ala Arg Gln Ala Ile Arg Ser Leu Thr Glu
1105                1110                1115                1120

CGG CTT TAT ATC GGG GGT CCC CTG ACT AAT TCA AAA GGG CAG AAC TGC                3408
Arg Leu Tyr Ile Gly Gly Pro Leu Thr Asn Ser Lys Gly Gln Asn Cys
                    1125                1130                1135

GGC TAT CGC CGG TGC CGC GCG AGC GGC GTG CTG ACG ACT AGC TGC GGT                3456
Gly Tyr Arg Arg Cys Arg Ala Ser Gly Val Leu Thr Thr Ser Cys Gly
                1140                1145                1150

AAT ACC CTC ACA TGT TAC TTG AAG GCC TCT GCA GCC TGT CGA GCT GCA                3504
Asn Thr Leu Thr Cys Tyr Leu Lys Ala Ser Ala Ala Cys Arg Ala Ala
            1155                1160                1165

AAG CTC CAG GAC TGC ACG ATG CTC GTG TGC GGA GAC GGC CTT GTC GTT                3552
Lys Leu Gln Asp Cys Thr Met Leu Val Cys Gly Asp Asp Leu Val Val
        1170                1175                1180

ATC TGT GAG AGC GCG GGA ACC CAG GAG GAC GCG GCG AGC CTA CGA GTC                3600
Ile Cys Glu Ser Ala Gly Thr Gln Glu Asp Ala Ala Ser Leu Arg Val
1185                1190                1195                1200

TTC ACG GAG GCT ATG ACT AGG TAC TCT GCC CCC CCC GGG GAC CCG CCC                3648
Phe Thr Glu Ala Met Thr Arg Tyr Ser Ala Pro Pro Gly Asp Pro Pro
                    1205                1210                1215

CAA CCA GAA TAC GAC CTG GAG TTG ATA ACA TCA TGC TCC TCC AAT GTG                3696
Gln Pro Glu Tyr Asp Leu Glu Leu Ile Thr Ser Cys Ser Ser Asn Val
                1220                1225                1230

TCG GTC GCG CAC GAT GCA TCT GGC AAA AGG GTA TAC TAC CTC ACC CGT                3744
Ser Val Ala His Asp Ala Ser Gly Lys Arg Val Tyr Tyr Leu Thr Arg
            1235                1240                1245

GAC CCG                                                                        3750
Asp Pro
1250
```

-continued (2) INFORMATION FOR SEQ ID NO:23:

(i) SEQUENCE CHARACTERISTICS:
        (A) LENGTH: 23 bases
        (B) TYPE: nucleotide
        (C) STRANDEDNESS: single
        (D) TOPOLOGY: linear (ii) MOLECULE TYPE: synthetic DNA (vi) ORIGINAL SOURCE:
        (A) ORGANISM: baculovirus AcNPV (vii) IMMEDIATE SOURCE:
        (A) LIBRARY: oligonucleotide synthesizer; oligo d24

(ix) FEATURE:
        (B) LOCATION: from 1 to 23 bases homologous to portion of
            AcNPV polyhedrin gene downstream of the BamH1 cloning
            site in pAc360 and similar vectors
        (D) OTHER INFORMATION: primes DNA synthesis from baculovirus
            transfer vector sequences which flank DNA inserted at the
            BamH1 site.

(xi) SEQUENCE DESCRIPTION: SEQ ID NO:23:

```
CGGGTTTAAC ATTACGGATT TCC                                              23
```

(2) INFORMATION FOR SEQ ID NO:24:

(i) SEQUENCE CHARACTERISTICS:
        (A) LENGTH: 31 bases
        (B) TYPE: nucleotide
        (C) STRANDEDNESS: single
        (D) TOPOLOGY: linear (ii) MOLECULE TYPE: synthetic DNA (vi) ORIGINAL SOURCE:
        (A) ORGANISM: baculovirus AcNPV (vii) IMMEDIATE SOURCE:
        (A) LIBRARY: oligonucleotide synthesizer; oligo d126

(ix) FEATURE:
        (B) LOCATION: from 1 to 31 bases homologous to the upstream
            junction sequences produced when cDNA amplified by d75
            (SEQ ID NO:5) is cloned into the BamH1 cloning site in
            pAc360 and similar vectors; mismatches at bases 13 and 14
            introduce a Pst1 site from 1 to 10 bases.
        (D) OTHER INFORMATION: primes DNA synthesis at the junction of
            baculovirus transfer vector sequences and sequences
            previously amplified by oligo d75; introduces a Pst1
            recognition site for subsequent cloning work (xi) SEQUENCE DESCRIPTION: SEQ ID NO:24:

```
TAAGGATCCC CCT GCA GTA TCG GCG GAA TTC                                 31
           Ser Ala Val Ser Ala Glu Phe
                            5
```

(2) INFORMATION FOR SEQ ID NO:25:

(i) SEQUENCE CHARACTERISTICS:
        (A) LENGTH: 46 bases
        (B) TYPE: nucleotide
        (C) STRANDEDNESS: single
        (D) TOPOLOGY: linear (ii) MOLECULE TYPE: synthetic DNA (vi) ORIGINAL SOURCE:
        (A) ORGANISM: N/A (vii) IMMEDIATE SOURCE:
        (A) LIBRARY: oligonucleotide synthesizer; oligo d132

```
    (ix) FEATURE:
        (B) LOCATION: form 5 to 10 bases Pst1 recognition site
            from 13 to 27 bases linker coding for five Lys residues
            from 28 to 45 bases homologous to bases 4 to 21 of BR11
        (SEQ ID NO:7)
        (D) OTHER INFORMATION: primes DNA synthesis at the 5' end of
            BR11 and introduces a synthetic sequence which codes for
            five lysines as well as a Pst1 recognition site for
            subsequent cloning work (xi) SEQUENCE DESCRIPTION: SEQ ID NO:25:

CTGCCTGCA GTA AAG AAG AAG AAG AAG AAA ACC AAA CGT AAC ACC A             46
          Val Lys Lys Lys Lys Lys Lys Thr Lys Arg Asn Leu
                           5                   10
```